US008754052B2

(12) United States Patent
Lieske et al.

(10) Patent No.: US 8,754,052 B2
(45) Date of Patent: Jun. 17, 2014

(54) TREATMENT OF NEPHROLITHIASIS AND UROLITHIASIS USING 1,2,3,4,6-PENTA-O-GALLOYL-BETA-D-GLUCOSE (PGG)

(75) Inventors: John C. Lieske, Rochester, MN (US); Sung-Hoon Kim, Seoul (KR)

(73) Assignee: Mayo Foundation for Medical Education and Research, Rochester, MN (US)

( * ) Notice: Subject to any disclaimer, the term of this patent is extended or adjusted under 35 U.S.C. 154(b) by 356 days.

(21) Appl. No.: 13/001,094

(22) PCT Filed: Jun. 25, 2009

(86) PCT No.: PCT/US2009/048639
§ 371 (c)(1),
(2), (4) Date: Jul. 26, 2011

(87) PCT Pub. No.: WO2009/158487
PCT Pub. Date: Dec. 30, 2009

(65) Prior Publication Data
US 2011/0275578 A1    Nov. 10, 2011

Related U.S. Application Data

(60) Provisional application No. 61/075,862, filed on Jun. 26, 2008.

(51) Int. Cl.
*A61K 31/7024* (2006.01)
*A61K 31/7028* (2006.01)
*A61K 31/7034* (2006.01)

(52) U.S. Cl.
USPC .......................................................... 514/25

(58) Field of Classification Search
USPC .................................................. 514/54, 25
See application file for complete search history.

(56) References Cited

U.S. PATENT DOCUMENTS 5,266,319 A * 11/1993 Cheng et al. .................... 514/23
7,273,951 B2    9/2007 Biessen et al.

FOREIGN PATENT DOCUMENTS

KR    10/2003/0075947    9/2003
KR    10/2005/0095287    9/2005
WO    WO 02/080951    10/2002
WO    WO 2007/137602    12/2007

OTHER PUBLICATIONS

Piao et al, Phytotherapy research, Apr. 2008, 22, 534-38.*
Selvam, R. Urol. Res. 2002, 30, 35-47.*
Verhulst et al, J. Am. Chem. Nephrol., 2003, 13, 107-115.*

Authorized Officer K.H. Song. International Search Report and Written Opinion in International Application No. PCT/US2009/048639, mailed Feb. 23, 2010, 12 pages.
Authorized Officer A. Nickitas-Etienne. International Preliminary Report on Patentability in International Application No. PCT/US2009/048639, mailed Jan. 5, 2011, 6 pages.
Afify et al., "Expression of hyaluronic acid and its receptors, CD44s and CD44v6, in normal, hyperplastic, and neoplastic endometrium," *Ann Diagn Pathol*, 2005; 9(6):312-8.
Ahn et al., "Effects of Oral Administration of Citrate, Thiazide, Allopurinol and Magnesium on Renal Calcium Oxalate Crystal Oxalate Crystal Formation and Osteopontin Expression in a Rat Urolithiasis Model," *Korean J. Urol.*, 2003, 44(1):87-94.
Atmani et al., "Extract from *Herniaria hirsuta* coats calcium oxalate monohydrate crystals and blocks their adhesion to renal epithelial cells," *J Urol.*, 2004; 172(4 Pt):1510-4.
Bhimani et al , "Inhibition of oxidative stress in HeLa cells by chemopreventive agents," *Cancer Res.*, 1993; 53(19):4528-33.
Brannon, "Green Tea: New Benefits from an Old Favorite," *Nutrition Dimension*, 2007, 1-26.
Campos and Schor, "*Phyllanthus niruri* inhibits calcium oxalate endocytosis by renal tubular cells: its role in nephrolithiasis," *Nephron*, 1999; 81: 393-397.
Erdelyi et al., "Gallotannin inhibits the expression of chemokines and inflammatory cytokines in A549 cells," *Mol Pharmacol.*, 2005; 68(3):895-904.
Farell et al., "Modulation of proliferating renal epithelial cell affinity for calcium oxalate monohydrate crystals," *J Am Soc Nephrol.*, 2004; 15(12):3052-62.
Flagg, "Dietary and holistic treatment of recurrent calcium oxalate kidney stones: review of literature to guide patient education," *Urol Nurs*, 2007, 27(2):113-22.
Grases et al., "Effect of *Herniaria hirsuta* and *Agropyron repens* on calcium oxalate urolithiasis risk in rats," *Journal of Ethnopharmacology*, 1995; 45:211-214.
Grases et al., "The influence of *Zea mays* on urinary risk factors for kidney stones in rats," *Phytotherapy Research*, 1993; 7:146-149.
Hadjzadeh et al., "Ethanolic extract of *Nigella sativa* L seeds on ethylene glycol-induced kidney calculi in rats," *Urol J.*, 2007; 4(2):86-90.
Hofmann and Gross, "Biosynthesis of gallotannins: formation of polygalloylglucoses by enzymatic acylation of 1,2,3,4,6-penta-O-galloylglucose," *Arch Biochem Biophys.*, 1990; 283(2):530-2.
Huh et al., "Penta-O-galloyl-beta-D-glucose suppresses tumor growth via inhibition of angiogenesis and stimulation of apoptosis: roles of cyclooxygenase-2 and mitogen-activated protein kinase pathways," *Carcinogenesis*, 2005; 26(8):1436-45.
Itoh et al., "Preventive Effects of Green Tea on Renal Stone Formation and the role of Oxidative stress in Nephrolithiasis," *J. Urol.*, 2005, 173(1):271-275.
Jeong et al., "Effects of green tea on urinary stone formation: an in vivo and in vitro study," *J Endourol.*, 2006; 20(5):356-61.
Ji et al., "Anticoagulant 1,2,3,4,6-pentagalloyl-beta-D-glucopyranose isolated from geranium (*Pelargonium inquinans* Ait)," *Arch Pharm Res.*, 2005; 28(9):1037-41.
Kang et al., "Vasodilatory and anti-inflammatory effects of the 1,2,3,4,6-penta-O-galloyl-beta-D-glucose (PGG) via a nitric oxide-cGMP pathway," *Eur J Pharmacol.*, 2005; 524(1-3):111-9.

(Continued)

*Primary Examiner* — Ganapathy Krishnan
(74) *Attorney, Agent, or Firm* — Fish & Richardson P.C.

(57) ABSTRACT

The treatment of nephrolithiasis or urolithiasis by methods that include administration of 1,2,3,4,6-penta-O-galloyl-beta-D-glucose (PGG) or a salt or derivative thereof, or a pharmaceutically acceptable composition comprising the same are provided herein.

27 Claims, 17 Drawing Sheets

(56) References Cited

OTHER PUBLICATIONS

Khan, "Interactions between stone-forming calcific crystals and macromolecules," *Urol Int.*, 1997; 59(2):59-71.

Khanbabaee and Ree, "Tannis: Classificatio and Definition," *Nat. Prod. Rep.*, 2001, 18:641-649.

Klein et al., "Antidiabetes and Anti-obesity Activity of *Lagerstroemia speciosa*," *eCam*, 2007, 4(4):401-407.

Kumar et al., "Urinary macromolecular inhibition of crystal adhesion to renal epithelial cells is impaired in male stone formers," *Kidney Int.*, 2005; 68(4):1784-92.

Lee et al., "1, 2, 3, 4, 6-penta-O-galloyl-beta-D-glucose attenuates renal cell migration, hyaluronan expression, and crystal adhesion," *European J of Pharmacology*, 2009, 606(1-3):32-37.

Micali et al., "Medical therapy of urolithiasis," *J Endourol.*, 2006; 20(11):841-7.

Oh et al., "In vitro anti-proliferative effect of 1,2,3,4,6-penta-O-galloyl-beta-D-glucose on human hepatocellular carcinoma cell line, SK-HEP-1 cells," *Cancer Left.*, 2001; 174(1):17-24.

Okubo et al., "The inhibition of phenylhydroquinone-induced oxidative DNA cleavage by constituents of Moutan Cortex and Paeoniae Radix," *Biol Pharm Bull.*, 2000; 23(2):199-203.

Park and Pearle, "Pathophysiology and management of calcium stones," *Urol Clin North Am*, 2007, 34(3):323-34.

Piao et al., "Antioxidative activity of geranium (*Pelargonium inquinans* Ait) and its active component, 1, 2, 3, 4, 6-penta-O-galloyl-beta-D-glucose," *Phytother Res.*, 2008, 22(4):534-538.

Porena et al., "Prevention of stone disease," *Urol Int.*, 2007; 79 Suppl 1:37-46.

Rabinovich et al., "Adhesion force between calcium oxalate monohydrate crystal and kidney epithelial cells and possible relevance for kidney stone formation," *J Colloid Interface Sci.*, 2006; 300(1):131-40.

Ren et al., "Synthesis and Structure—Activity Relationship Study of Antidiabetic Penta-O-galloyl-D-glucopyranose and Its Analogues," *J Med Chem.*, 2006, 49(9):2829-2837.

Riese et al., "Cell polarity and calcium oxalate crystal adherence to cultured collecting duct cells," *Am J Physiol.*, 1992; 262(2 Pt 2):F177-84.

Selvam, "Calcium oxalate stone disease: role of lipid peroxidation and antioxidants," *Urol Res.*, 2002; 30(1):35-47.

Sheng et al., "Adhesion at calcium oxalate crystal surfaces and the effect of urinary constituents," *Proc Natl Acad Sci*, 2005; 102(2):267-72.

Stern, "Hyaluronan catabolism: a new metabolic pathway," *Eur J Cell Biol.*, 2004; 83(7):317-25.

Tsujihata et al., "Atorvastatin Inhibits Renal Crystal Retention in a Rate Stone Forming Model," *J. Urol.*, 2008, 180(5):2212-2217.

Verhulst et al., "Crystal retention capacity of cells in the human nephron: involvement of CD44 and its ligands hyaluronic acid and osteopontin in the transition of a crystal binding—into a nonadherent epithelium," *J Am Soc Nephrol.*, 2003; 14(1):107-15.

Verkoelen and Verhulst, "Proposed mechanisms in renal tubular crystal retention," *Kidney Int.*, 2007; 72(1):13-8.

Zhao et al., "The isolation of 1,2,3,4,6-penta-O-galloyl-beta-D-glucose from *Acer truncatum* Bunge by high-speed counter-current chromatography," *J Chromatogr B Analyt Technol Biomed Life Sci.*, 2007; 850(1-2):523-7.

\* cited by examiner

TREATMENT OF NEPHROLITHIASIS AND UROLITHIASIS USING 1,2,3,4,6-PENTA-O-GALLOYL-BETA-D-GLUCOSE (PGG)

CROSS-REFERENCE TO RELATED APPLICATIONS

This application is a National Stage application under 35 U.S.C. §371 and claims the benefit under 35 U.S.C. §119(a) of International Application No. PCT/US2009/048639, having an International Filing Date of Jun. 25, 2009, which claims the benefit of U.S. Provisional Application Ser. No. 61/075,862, having a filing date of Jun. 26, 2008, all of which are incorporated herein in their entirety.

TECHNICAL FIELD

This disclosure relates to the treatment of nephrolithiasis or urolithiasis by methods that include administration of 1,2,3,4,6-penta-O-galloyl-beta-D-glucose (PGG) or a salt or derivative thereof.

BACKGROUND

The formation of crystal aggregates in the urinary tract can result in kidney and bladder stones, clinical conditions referred to as nephrolithiasis or urolithiasis. Kidney and bladder stones are the result of the aggregation or growth of dissolved minerals normally present in the urine. Crystals form in urine that is supersaturated with particular salts such as calcium oxalate, sodium urate, magnesium ammonium phosphate, or cystine. Calcium oxalate monohydrate is the most common component of kidney stones and its crystals are present in 70% of all nephrolithiasis and urolithiasis cases. These conditions occur most often in the third to fifth decade of life, and more often in men than women. Although there are currently treatments for nephrolithiasis and urolithiasis, many therapeutic strategies only reduce stone recurrence by approximately half.

SUMMARY

Provided herein is a method of treating nephrolithiasis and urolithiasis in a subject by administering an effective amount of 1,2,3,4,6-penta-O-galloyl-beta-D-glucose (PGG) or a salt or derivative thereof. In some embodiments, PGG reduces or inhibits binding of renal calculi to renal cells. In some embodiments, PGG reduces hyaluronan expression in renal cells. In some embodiments, PGG reduces proliferative and/or migratory activity of renal cells.

Further provided herein is a method of reducing binding of renal calculi to renal cells in a subject, the method comprising administering to the subject a therapeutically effective amount of PGG, or a salt or derivative thereof.

Renal calculi can comprise one or more of calcium oxalate, struvite, urate, calcium phosphate, cystine, silicate, xanthine, and triamterene. In some embodiments, calcium oxalate can be selected from calcium oxalate monohydrate and calcium oxalate dihydrate.

Renal cells can be selected from renal epithelial cells and renal endothelial cells. In some embodiments, the renal epithelial cells can be renal tubular epithelial cells. In some embodiments, the renal cells can be proliferating, migrating, under oxalate-induced peroxidative injury, or wound damaged.

In some embodiments, the PGG reduces hyaluronan expression in the renal cells, such as cell-surface expression.

A method of treating nephrolithiasis or urolithiasis in a subject is also provided herein, the method comprising administering to the subject a therapeutically effective amount of PGG, or a salt or derivative thereof.

Provided herein is a method of inhibiting binding of renal calculi to renal cells in a subject, the method comprising administering to the subject a therapeutically effective amount of PGG, or a salt or derivative thereof.

Further provided is a method of reducing hyaluronan expression in renal cells in a subject, the method comprising administering to the subject a therapeutically effective amount of PGG, or a salt or derivative thereof. In some embodiments, the hyaluronan is expressed on the cell surface. In some embodiments, the renal cells can be selected from renal epithelial cells (e.g., renal tubular epithelial cells) and renal endothelial cells. In some embodiments, the renal cells can be proliferating, migrating, under oxalate-induced peroxidative injury, or wound damaged.

A method of reducing proliferative and/or migratory activity of renal cells in a subject is provided, the method comprising administering to the subject a therapeutically effective amount of PGG, or a salt or derivative thereof. In some embodiments, the migratory activity can be repair migration. In some embodiments, the proliferative and/or migratory activity is activated by physical injury.

Also provided herein is a pharmaceutical composition comprising a pharmaceutically acceptable carrier and PGG, or a salt or derivative thereof.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 4A illustrates the effect of PGG on [$^{14}$C]COM crystal adhesion to MDCK I cells. FIG. 4B illustrates the effect of PGG precoating of [$^{14}$C]COM crystals on their subsequent adhesion to MDCK I cells compared with a control.

DETAILED DESCRIPTION

I. Definitions

Figure 1:
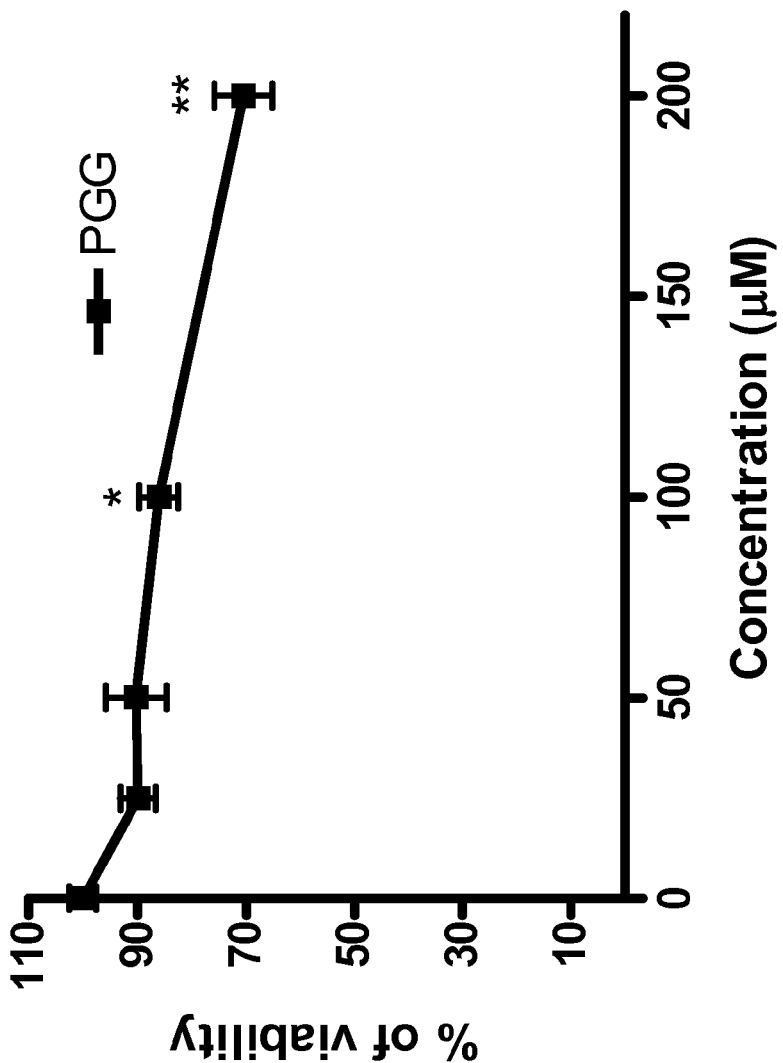
FIG. 1 illustrates the lack of cytotoxicity of PGG on MDCK I cells except at high concentrations.

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

The term "contacting" means bringing at least two moieties together, whether in an in vitro system or an in vivo system.

The expression "effective amount," when used to describe an amount of compound applied in a method, refers to the amount of a compound that achieves the desired pharmacological effect or other effect, for example an amount that reduces the binding of renal calculi resulting in a useful effect.

The terms "treating" and "treatment" mean causing a therapeutically beneficial effect, such as ameliorating existing symptoms, preventing additional symptoms, ameliorating or preventing the underlying causes of symptoms, postponing or preventing the further development of a disorder and/or reducing the severity of symptoms that will or are expected to develop.

As used herein, "subject" (as in the subject of the treatment) means both mammals and non-mammals. Mammals include, for example, humans; non-human primates, e.g. apes and monkeys; cattle; horses; sheep; rats; mice; pigs; and goats. Non-mammals include, for example, fish and birds.

II. Pharmaceutical Compositions

Provided herein are pharmaceutical compositions comprising 1,2,3,4,6-penta-O-galloyl-beta-D-glucose (PGG) and pharmaceutically acceptable salt forms or derivatives thereof. A pharmaceutical composition can include PGG, or a salt or derivative thereof, and a pharmaceutically acceptable carrier.

PGG is a polyphenolic and water soluble gallotannin which can be isolated from the gallnut of *Rhus chinensis* MILL, *Acer truncatum* Bunge, *Pelargonium inquinans* Ait, and *Paeonia lactiflora* Pall. PGG has the following structure:

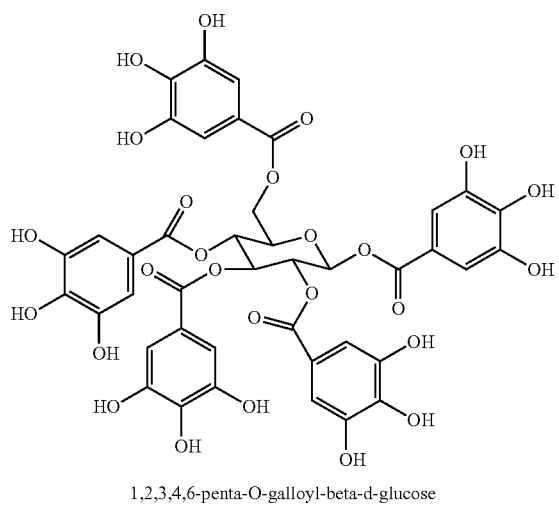 [SMILES: O=C(OCC1OC(OC(=O)c2cc(O)c(O)c(O)c2)C(OC(=O)c2cc(O)c(O)c(O)c2)C(OC(=O)c2cc(O)c(O)c(O)c2)C1OC(=O)c1cc(O)c(O)c(O)c1)c1cc(O)c(O)c(O)c1]

1,2,3,4,6-penta-O-galloyl-beta-d-glucose

PGG can be synthesized using conventional techniques using readily available starting materials. In general, PGG is conveniently obtained via standard organic chemistry synthesis methods. For example, PGG may be prepared using the following synthetic protocol (see Ren Y, Himmeldirk K, Chen X. *J Med. Chem.* 2006; 49(9):2829-37):

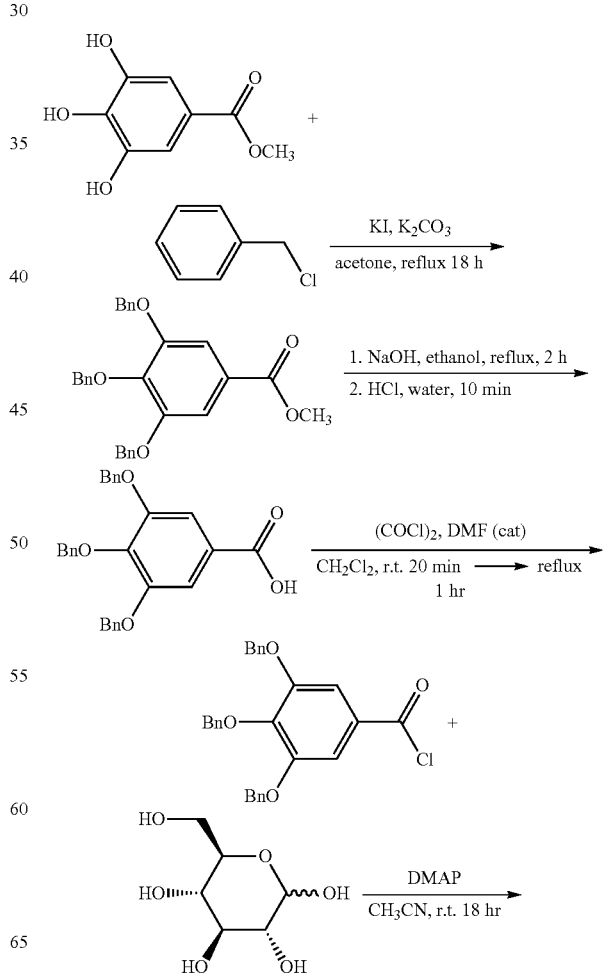

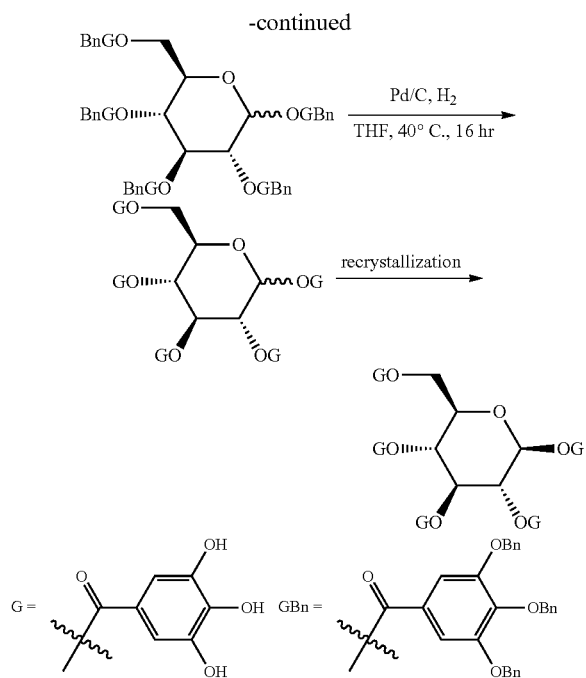

The term "pharmaceutically-acceptable salt" refers to salts which possess toxicity profiles within a range that affords utility in pharmaceutical applications. Pharmaceutically unacceptable salts may nonetheless possess properties such as high crystallinity, which may render them useful, for example in processes of synthesis, purification or formulation of PGG or a derivative thereof. In general the useful properties of PGG does not depend critically on whether the compound is or is not in a salt form, so unless clearly indicated otherwise (such as specifying that the compound should be in "free base" or "free acid" form), reference in the specification to PGG should be understood as encompassing salt forms of the compound, whether or not this is explicitly stated.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding PGG compound by reacting, for example, the appropriate acid or base with PGG. Preferably the salts are in crystalline form, and preferably prepared by crystallization of the salt from a suitable solvent. A person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

Pharmaceutical compositions described herein comprise PGG and a pharmaceutically acceptable carrier, excipient, or diluent. In some embodiments the pharmaceutical compositions provided herein contain PGG in an amount that is useful in the treatment of nephrolithiasis and/or urolithiasis.

Pharmaceutical carriers suitable for administration of the compounds provided herein include any such carriers known to those skilled in the art to be suitable for the particular mode of administration. Pharmaceutically acceptable carriers, excipients, and diluents include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α, β, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of compounds of the formulae described herein. In some embodiments, the carrier, excipient, or diluent is a physiologically acceptable saline solution.

III. Methods of Use

Provided herein is a method of treating nephrolithiasis in a subject by administering an effective amount of 1,2,3,4,6-penta-O-galloyl-beta-D-glucose (PGG) or a salt or derivative thereof, or a composition comprising the same. Further provided is a method of treating urolithiasis in a subject by administering an effective amount of PGG or a salt or derivative thereof, or a composition comprising the same.

A method of reducing or inhibiting binding of renal calculi to renal cells in a subject is also provided. The method includes administering to the subject a therapeutically effective amount of PGG, or a salt or derivative thereof, or a composition comprising the same.

Renal calculi are solid crystal aggregations of dissolved minerals in urine that typically form inside the kidneys or bladder. These structures can be composed of one or more of calcium oxalate (e.g., calcium oxalate monohydrate and calcium oxalate dihydrate); struvite (e.g., magnesium, ammonium, or phosphate struvite); urate or uric acid; calcium phosphate; cysteine; silicate; xanthine; and triamterene. In some embodiments, a renal calculi can be composed of calcium oxalate. In some embodiments, a renal calculi can be composed of calcium oxalate monohydrate.

Renal cells, as described herein, can include renal epithelial cells and renal endothelial cells. In some embodiments, the renal cells can be renal epithelial cells (e.g., renal tubular epithelial cells). In some embodiments, the renal cells can be proliferating. In some embodiments, the renal cells can be migrating. In some embodiments, the renal cells can be under oxalate-induced peroxidative injury. In some embodiments, the renal cells can be wound damaged.

Without being bound by theory, one mechanism of treatment of nephrolithiasis and urolithiasis results from the ability of PGG to coat crystals that form renal calculi, thereby reducing or inhibiting binding of the crystals to the renal cells.

Hyaluronan is thought to be a binding molecule for crystals that form renal calculi. Provided herein is a method of reducing hyaluronan expression of a cell comprising contacting the cell with PGG, or a salt or derivative thereof, or a composition comprising the same. The method of reducing hyaluronan expression of a cell may be performed by contacting the cell with PGG, or a salt or derivative thereof, in vitro, thereby reducing hyaluronan expression of a cell. Uses of such an in vitro method of reducing hyaluronan expression include, but are not limited to use in a screening assay (for example, wherein PGG is used as a positive control or standard compared to compounds of unknown activity or potency in reducing hyaluronan expression). In some embodiments, the hyaluronan expression is reduced in a renal cell.

The method of reducing hyaluronan expression in a cell may be performed by contacting the cell with PGG, or a salt form thereof, in vivo, thereby reducing hyaluronan expression. The contacting is achieved by causing PGG, or a salt form thereof, to be present in the subject in an effective amount to achieve reduction of hyaluronan expression. This may be achieved, for example, by administering an effective amount of PGG, or a pharmaceutically acceptable salt form thereof, to the subject, or by administering a prodrug of PGG, or a pharmaceutically acceptable salt form thereof. Uses of such an in vivo method of reducing hyaluronan expression include, but are not limited to use in methods of treating a disease or condition, wherein reduction of hyaluronan is beneficial, or treating or preventing diseases, wherein hyaluronan expression contributes to the pathology and/or symptomology of the disease. In some embodiments, hyaluronan expression is reduced in a renal cell, for example in a patient suffering from nephrolithiasis or urolithiasis. The method is preferably performed by administering an effective amount of PGG, or a pharmaceutically acceptable salt form thereof, or a composition comprising the same, to a subject who is suffering from nephrolithiasis or urolithiasis.

Further provided herein is a method of reducing proliferative and/or migratory activity of renal cells in a subject. The method includes administering to the subject a therapeutically effective amount of PGG, or a salt or derivative thereof, or a composition comprising the same. In some embodiments, the migratory activity is repair migration. In some embodiments, the proliferative and/or migratory activity is activated by physical injury or physical activity of the cells.

Also provided herein is a method of reducing proliferative and/or migratory activity of a cell comprising contacting the cell with PGG, or a salt or derivative thereof. The method of reducing proliferative and/or migratory activity of a cell may be performed by contacting the cell with PGG, or a salt or derivative thereof, in vitro, thereby reducing proliferative and/or migratory activity of a cell in vitro. Uses of such an in vitro method of reducing proliferative and/or migratory activity include, but are not limited to use in a screening assay (for example, wherein PGG is used as a positive control or standard compared to compounds of unknown activity or potency in reducing proliferative and/or migratory activity). In some embodiments, the proliferative and/or migratory activity is reduced in a renal cell.

The method of reducing proliferative and/or migratory activity of a cell may be performed by contacting the cell with PGG, or a salt form thereof, in vivo, thereby reducing proliferative and/or migratory activity, in vivo. The contacting is achieved by causing PGG, or a salt form thereof, to be present in the subject in an effective amount to achieve reduction of proliferative and/or migratory activity. This may be achieved, for example, by administering an effective amount of PGG, or a pharmaceutically acceptable salt form thereof, to the subject, or by administering a prodrug of PGG, or a pharmaceutically acceptable salt form thereof. Uses of such an in vivo method of reducing proliferative and/or migratory activity include, but are not limited to use in methods of treating a disease or condition, wherein reducing proliferative and/or migratory activity is beneficial, or treating or preventing diseases, wherein proliferative and/or migratory activity contributes to the pathology and/or symptomology of the disease. In some embodiments, proliferative and/or migratory activity is reduced in a renal cell, for example in a patient suffering from nephrolithiasis or urolithiasis. The method is preferably performed by administering an effective amount of PGG, or a pharmaceutically acceptable salt form thereof, or a composition comprising the same, to a subject who is suffering from nephrolithiasis or urolithiasis.

PGG can also be administered in combination with existing methods of treating nephrolithiasis and/or urolithiasis, for example potassium citrate, thiazides such as hydrochlorothiazide and allopurinol. In some embodiments, PGG can be administered in combination with a procedure called lithotripsy (i.e., wherein shock waves are used to break up a large stone into smaller pieces that can then pass through the urinary system), in order to prevent retention of fragments in the kidney. In some embodiments, PGG can be administered in combination with surgical techniques which have also been developed to remove kidney stones, such as percutaneous nephrolithotomy. In some embodiments, PGG can be administered before, during, or after another nephrolithiasis or urolithiasis agent or treatment. In some embodiments, PGG (or a pharmaceutically acceptable salt form or derivative thereof) can be administered in combination with (i.e., before, during, or after) administration of a pain relief agent (e.g., a nonsteroidal anti-inflammatory drug such as celecoxib or rofecoxib).

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers (see, e.g., Ansel Introduction to Pharmaceutical Dosage Forms, Fourth Edition 1985, 126).

The concentration of PGG in a pharmaceutical composition will depend on absorption, inactivation and excretion rates of the compound, the physicochemical characteristics of the compound, the dosage schedule, and amount administered as well as other factors known to those of skill in the art. For example, the amount that is delivered is sufficient to treat nephrolithiasis and/or urolithiasis, as described herein.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of PGG or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing PGG and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing PGG in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

EXAMPLES

General Methods

Calcium oxalate monohydrate (COM) crystals were prepared from supersaturated solutions. To prepare radioactive COM crystals, [$^{14}$C]oxalic acid (30-60 mCi/mmol; ICN Biomedicals, Irivine, Calif., USA) was added to a sodium oxalate solution, producing a specific activity of $10^5$ cpm/mL, and sufficient calcium chloride was then added to form a supersaturated solution. The precipitated COM crystals had a specific activity of 300 to 450 cpm/μg. Dulbecco-Vogt modified Eagle's essential medium (DMEM; GIBCO, Life Technologies Inc., NY), antibiotic-antimycotics were purchased from GIBCO (Grand island, NY). Fetal bovine serum (FBS) was from JRH (Lenexa, Kans.). HEPES (N-[2-hydroxyethyl]piperazine-N'-[2-ethanesulfonic acid]), sodium bicarbonate, MTT (3-(4,5-dimethylthiazol-2-yl)-2,5-diphenyltetrazolium bromide, BSA (bovine serum albumin were obtained from Sigma Chemical Co. (St. Louis, Mo.).

A. Isolation and Identification of PGG from Gallunt of *Rhus chinensis* MILL

Gallunt of *Rhus chinensis* MILL was obtained from the Oriental Medical Hospital of Kyunghee University in Seoul. A methanol (MeOH) extract (252 g) was dissolved in distilled water (800 mL), and successively fractionated with equal volumes of n-hexane, ethyl acetate (EtOAc) and butanol with water. The butanol fraction (35 g) was subject to silica gel column chromatography and eluted using chloroform, MeOH and $H_2O$ (65:35:10) and EtOAc, MeOH and $H_2O$ (100:15.6:13.5), followed by purification using HPLC (J' sphere ODS-HP80, 250×20 mm ID, S-4 μm, 80A, EtOAc:MeOH:$H_2O$=6:3:1). The active compound was identified as PGG (MW=986 g/mol) by NMR and FAB-MS analysis. The purity of PGG was estimated to be >98%. PGG was dissolved in dimethylsulfoxide (DMSO) for use in the in vitro studies that follow.

B. Cell Culture

Renal epithelial cells were of the Madin-Darby Canine kidney (MDCK) line, type I, derived from the distal nephron. Cells were grown in DMEM containing 25 mmol/L glucose at 37° C. in a humidified atmosphere containing 13% $CO_2$. To prepare high-density, quiescent cultures at $1\times10^6$ cells/35-mm plastic plate (9.62 cm$^2$; Nunc, Naperville, Ill., USA) were performed in DMEM containing 10% fetal bovine serum. Two days later when the cells were confluent, the established monolayer was used in the examples that follow.

Example 1

Cytotoxicity Assay

The effect of PGG on cytotoxicity against MDCK 1 cells was evaluated using a MTT (3-(4,5-dimethylthiazol-2-yl)-2,5-diphenyltetrazolium bromide) colorimetric assay. PGG was dissolved with dimethylsulfoxide (DMSO). The cells were seeded onto 96-well microplates at a density of $1\times10^4$ cells per well in 100 μL of DMEM containing 10% fetal bovine serum. After incubation at 37° C. in a humidified incubator for 24 h, cells were treated with various concentrations (50, 100, 150 and 200 μM) of PGG in serum-free DMEM for 24 h. After incubation, 50 μL of MTT (1 mg/ml in PBS) solution was added. Cells were incubated at 37° C. for 1 h and the optical density was measured using a microplate reader (Molecular Devices Co.) set at 570 nm. Cell viability was calculated as the percentage of viable cells in the PGG treated group versus those in the untreated control group using the following equation: cell viability (%)=[OD (PGG)−OD (Blank)/OD (Control)−OD (Blank)]×100.

As shown in FIG. 1, PGG did not exert any significant cytotoxicity against MDCK I cells in concentrations up to 25 uM. Therefore, nontoxic concentrations below 25 uM of PGG were used in subsequent experiments.

Example 2

Wound Healing Assay

MDCK I cells were seeded in a 35-mm plastic plate to confluent status overnight and incubated with serum-free medium for 6 h. A plastic pipette tip (200 μl size) was used to scrape a line between the MDCK1 cells that was approximately 2 to 3 mm wide across the entire culture dish. The medium was replaced by serum-free medium including various concentrations (1, 5 and 10 μM) of PGG. After incubation at 37° C. for 24 h, each plate was photographed (100×) and quantified.

Figure 2:
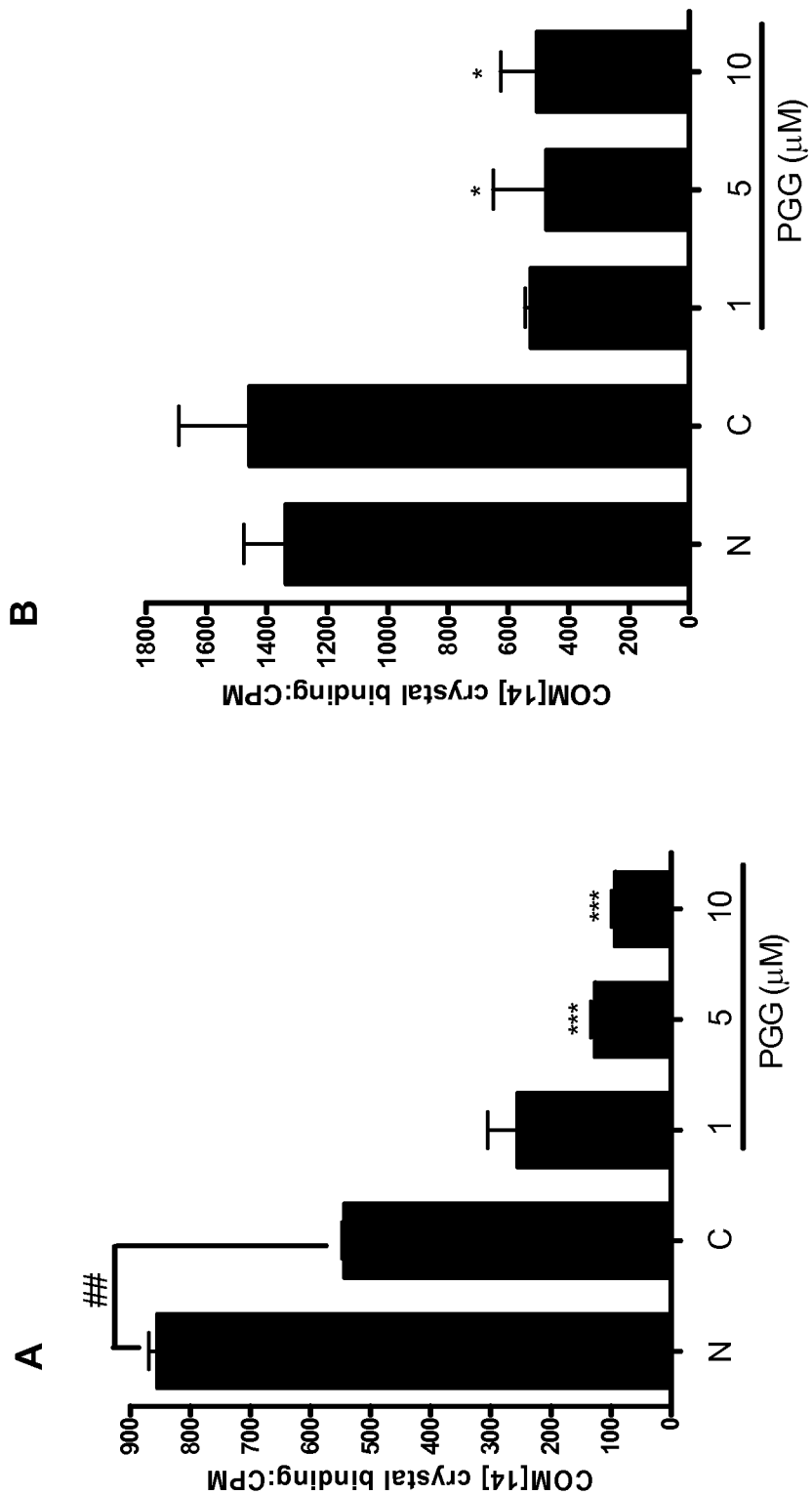
FIG. 2 illustrates the effect of PGG on COM crystal binding to wounded MDCK I cells.
Figure 3:
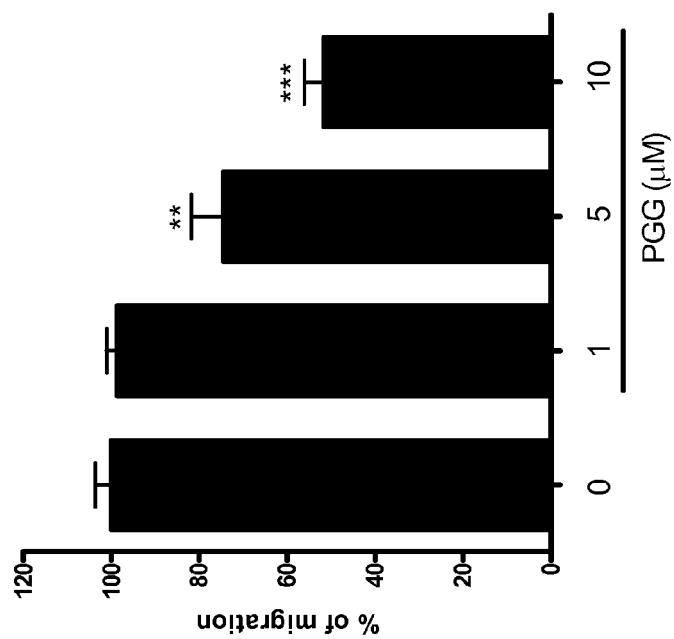
FIG. 3 details the effect of PGG on the migratory activity of MDCK I cells.
Figure 3:
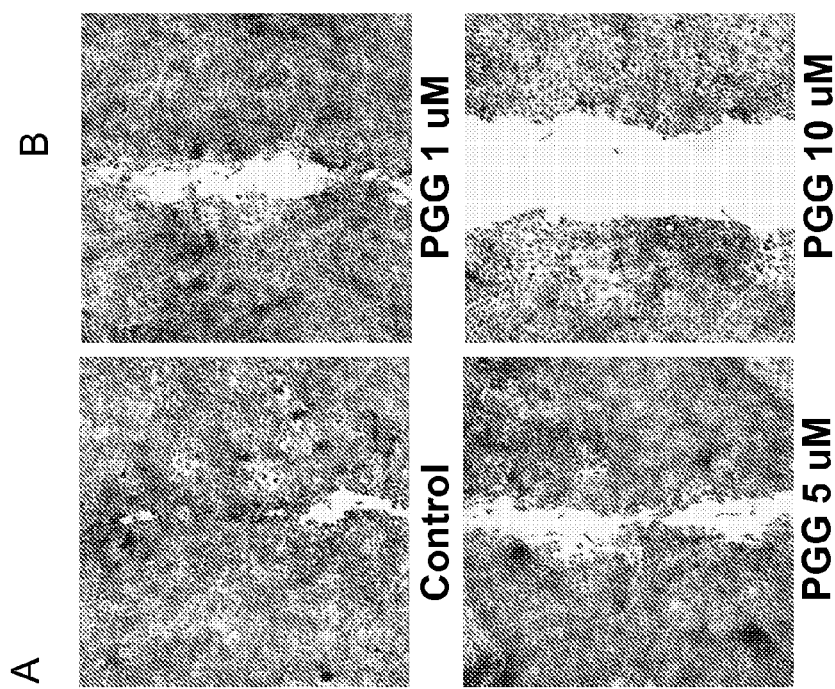

As shown in FIGS. 2A and 2B, PGG significantly inhibited COM adhesion to scrape-wounded MDCK I cells after 15 min or 24 h incubation time. In FIG. 3 it is shown that PGG significantly decreased migration after scrape wounding in a concentration dependent manner, inhibiting wound healing 2%, 26% and 49% at 1, 5 and 10 μM of PGG, respectively. These concentrations are in the range were affects were seen on crystal adhesion (FIG. 1).

Example 3

COM Crystal Binding Assay

MDCK I cells were treated with various concentrations (1, 5 and 10 μM) of PGG for 15 min or 24 h with and without wound damage and washed with phosphate-buffered saline (PBS, pH 7.4). Then [$^{14}$C] calcium oxalate monohydrate (COM) crystals were added to MDCK 1 cells, until a final concentration of 200 μg/mL (41.6 μg/cm$^2$ of cells) was achieved. The culture dishes were gently agitated for 5 seconds to uniformly distribute the crystals so that they settled to the surface of the cell monolayer under the force of gravity. After 2 min, the buffer was aspirated and the cells were washed 3 times with PBS. The cells and adherent crystals were then liquefied in 1 mL of 10% NaOH for 1 h and transferred to a scintillation vial containing 4.5 mL of Ecoscient (National Diagnostics, E. Palmetto, Fla., USA). The amount of radioactivity was measured, as described previously (See Riese, R. J. et al. Am J. Physiol (1992) 262: F177-84). Similarly, to precoat the [$^{14}$C]COM crystals with PGG, 0.4 mg [$^{14}$C]COM crystals were placed in a 5-mL tube containing 2 mL of a solution containing various concentrations (1, 5 and 10 μM) of PGG diluted in PBS. The crystals were incubated under end-over-end rotation for 15 min at room temperature, pelleted by centrifugation at 2,000 r.p.m. for 5 min, washed with PBS and then resuspended in 2 mL PBS. Two minutes later, the crystal binding activity was measured as described above.

Figure 4:
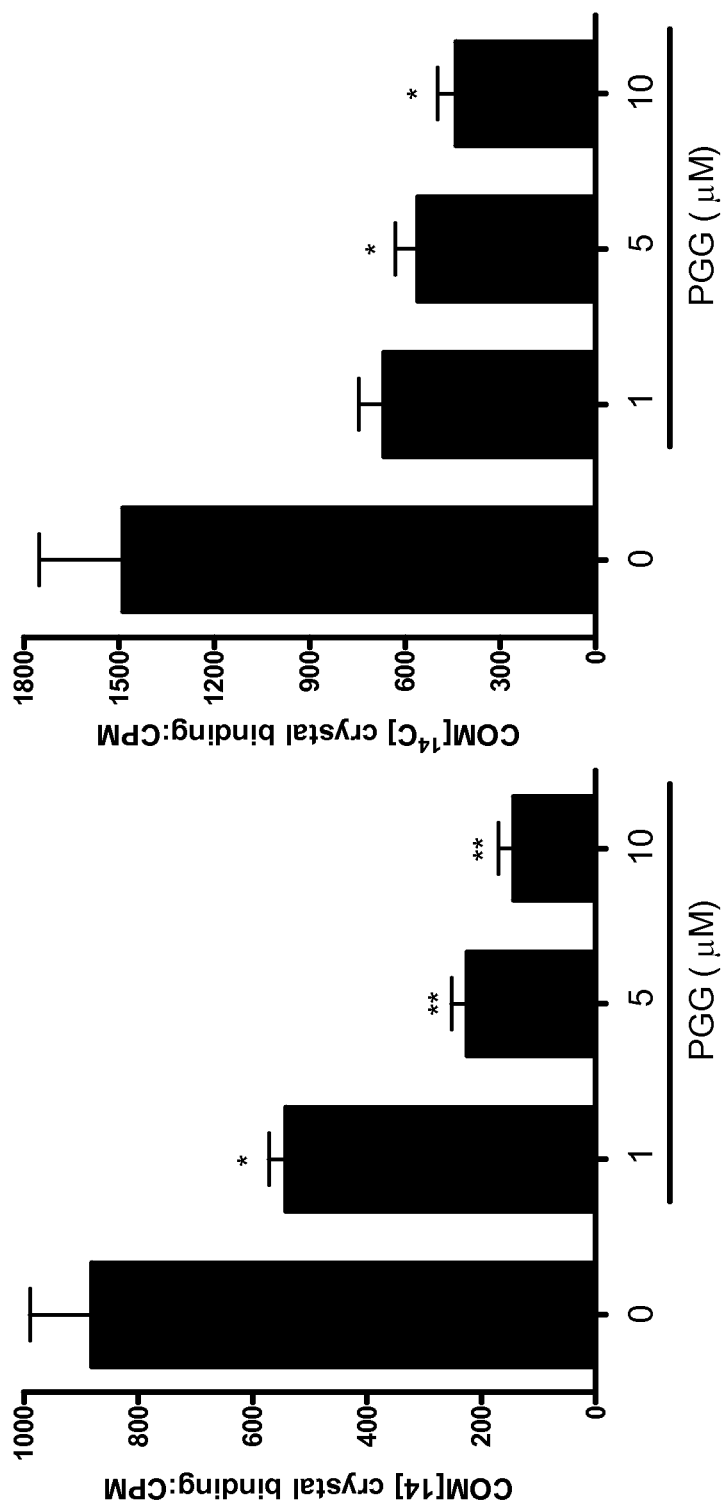
FIG. 4 details the effect of PGG on calcium oxalate monohydrate (COM) crystal binding to MDCK I cells.
Figure 5:
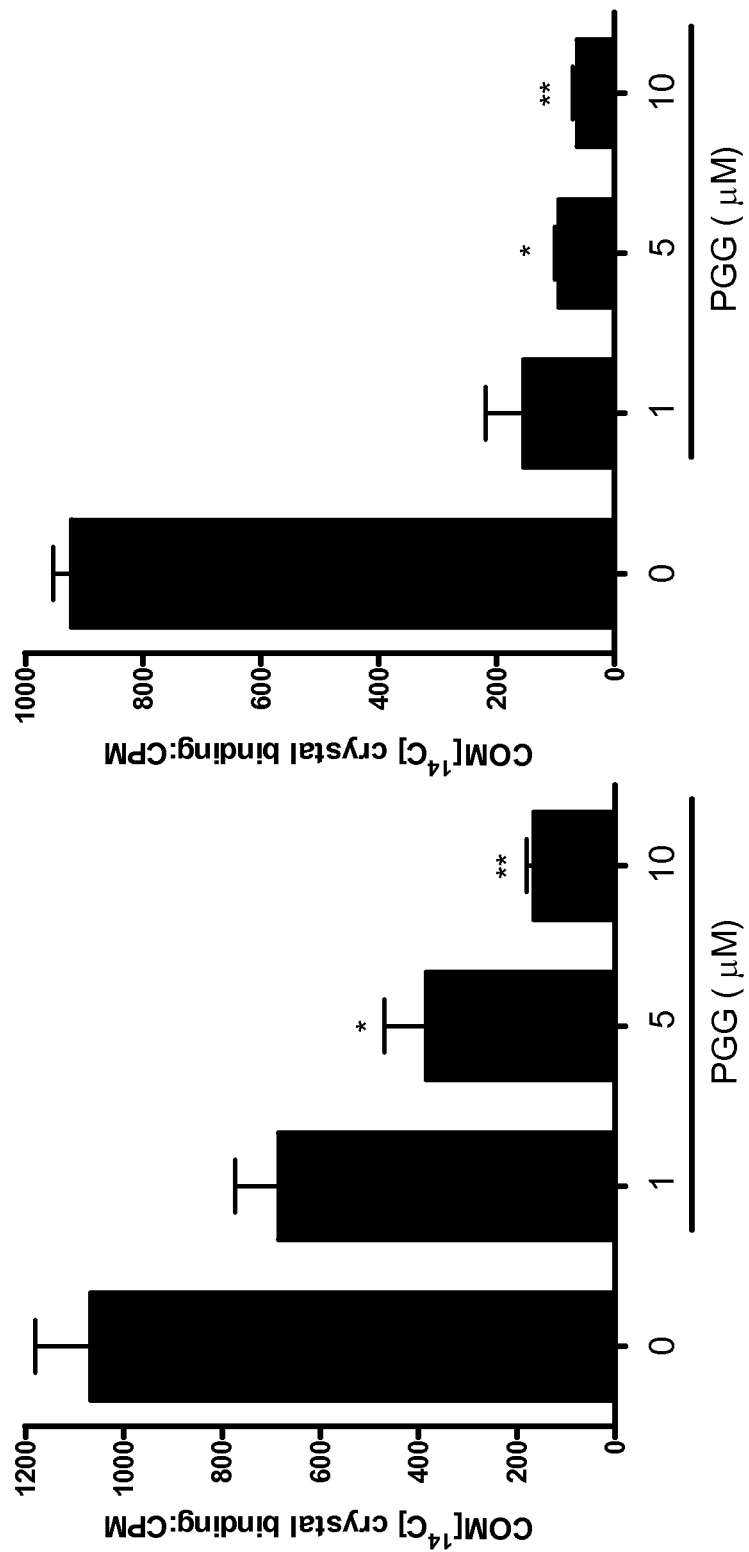
FIG. 5 shows the effect of PGG pretreatment of MDCK I cells for 15 minutes or 24 hours on the subsequent adhesion of [$^{14}$C]COM crystals.

As shown in FIG. 4A, addition of PGG to the buffer significantly reduced COM crystal adhesion to MDCK I cells in a concentration-dependent manner. FIG. 4B demonstrates that PGG effectively precoated the crystals in a concentration-dependent manner to decrease their subsequent binding to cells. Results of precoating the MDCK I cells demonstrated that PGG-pretreated cells subsequently bound less crystals (FIG. 5), whether pretreated for as little as 15 minutes or as much as 24 hours. Accordingly, PGG appeared to exert effects at both the cell and crystal level.

Example 4

Detection of Hyaluronan Expression by Confocal Microscopy and Western Blot

A middle line was scraped in the confluent MDCK 1 cells grown on coverslips using a 200 μL plastic pipette tip. The MDCK I cells on coverslips were then exposed to various concentrations (1, 5 and 10 μM) of PGG for 15 minutes or 24 hours at 37° C. The coverslips were rinsed three times with PBS, and fixed using 3.7% formaldehyde in PBS for 15 min. Cells were then rinsed three times with PBS and incubated with 1% goat serum for 1 h to block nonspecific binding sites. The goat serum was aspirated and the cells were incubated for 1 hour in a humidified chamber at 37° C. with biotinylated HABP. The cells were then washed with PBS (10 min×3) and then incubated 1 h with an avidin-conjugated Texas red (Molecular Probes, Eugene, Oreg.) in a humidified chamber at 37° C. Cells were again washed with PBS (10 min×3), and the coverslips were mounted onto glass slides using Slow-Fade (Molecular Probes, Eugene, Oreg.). The XZ section was scanned using a LSM 510 confocal microscope (Carl Zeiss, Oberkochen, Germany) equipped with an Axiovert 100M microscope and a c-Apochromat 63/1.2 numerical aperture water-immersion lens. Texas red was excited at 568-nm of an argon-krypton laser and the Emission for Texas red was collected at >585 nm.

For Western blotting, MDCK-I cells with or without scrape-wounding 24 hours earlier were harvested and washed with cold PBS; PGG (1, 5, 10 μM) was added to the medium 15 min or 24 hours prior to harvest. Cells were incubated in lysis buffer (50 mM Tris-HCl (pH 7.4), 150 mM NaCl, 1% Triton X-100, 0.1% SDS and 1 mM EDTA) supplemented with protease inhibitors (10 mg/ml leupeptin, 10 mg/ml aprotinin, 10 mg/ml pepstatin A and 1 mM of 4-(2-aminoethyl) benzenesulfonyl fluoride) and phosphatase inhibitors (1 mM NaF and 1 mM Na$_3$VO4) for 20 min on ice. Lysates were centrifuged at 14,000 g for 20 min at 4° C. Lysates containing 20 mg of protein were fractionated by SDS-PAGE and electrotransferred to a Hybond ECL transfer membrane (Amersham Pharmacia, Arlington Heights, Ill.). The blocked membranes were then incubated with primary antibodies (1:200 dilution) of HABP. After three successive washes with TBST for 10 min, the membrane was incubated with anti-biotin Horseradish Peroxidase (HRP)-conjugated antibody (1:1000 dilution). Bands were visualized using enhanced chemiluminescence (ECL).

Figure 6A:
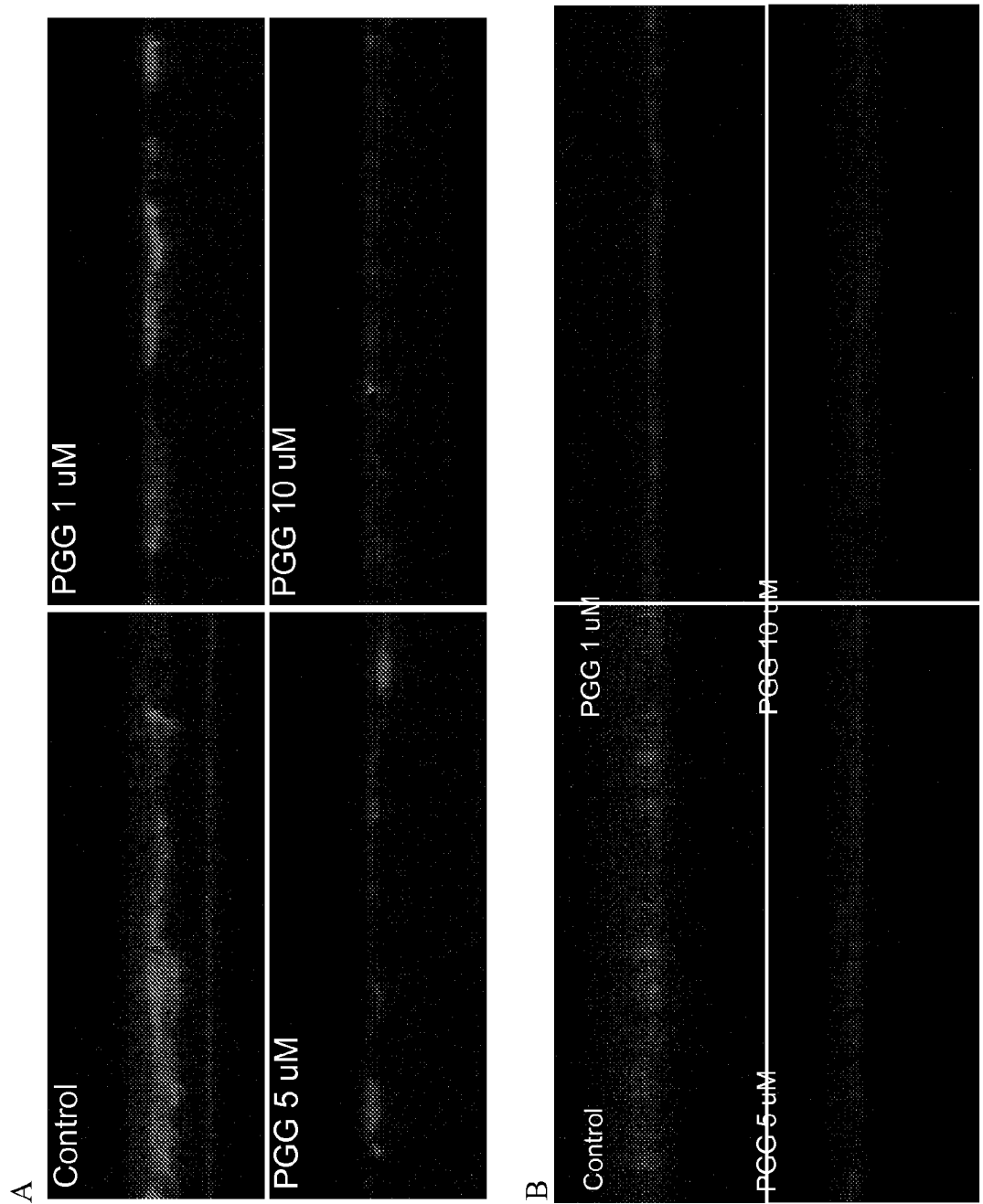
FIG. 6A shows the effect of PGG treatment for 15 minutes or 24 hours on hyaluronan expression on the surface of MDCK I cells by confocal microscopy.
Figure 6B:
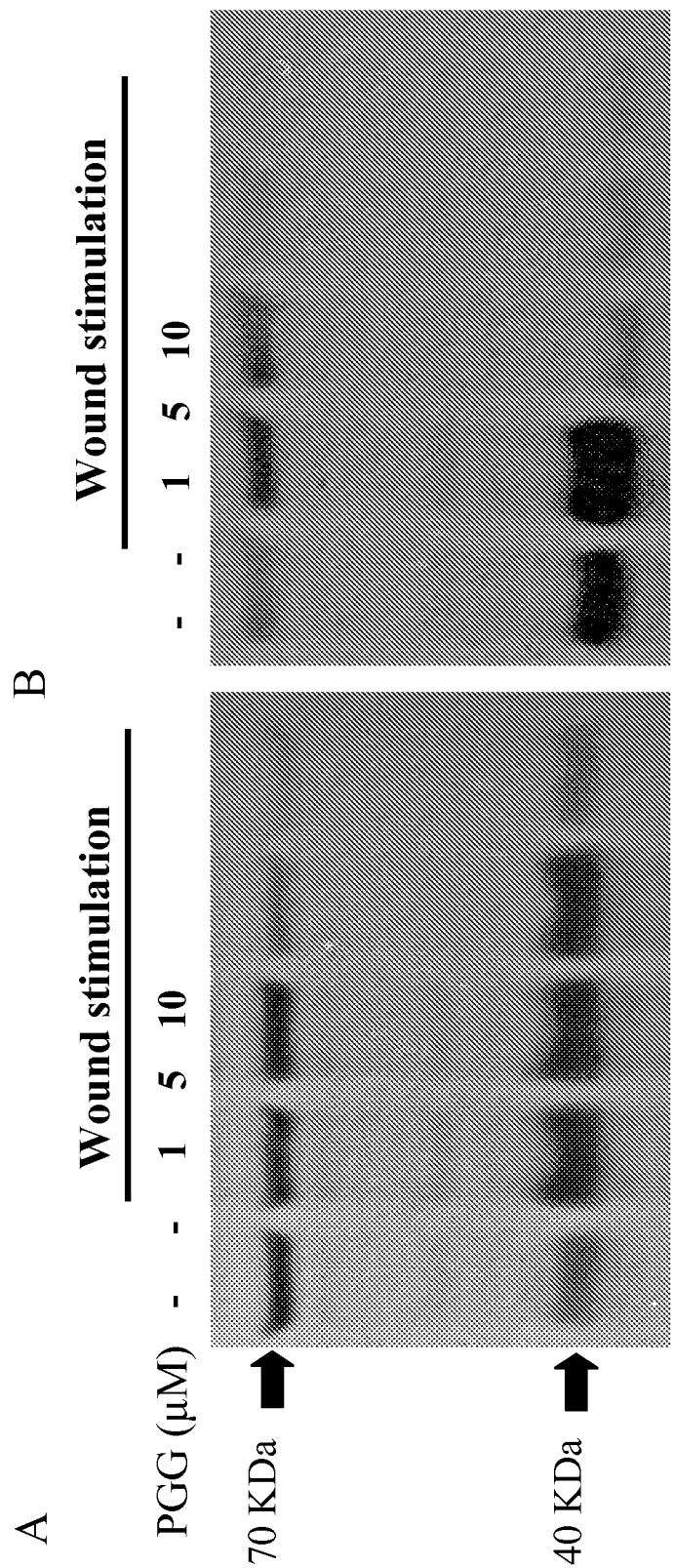
FIG. 6B shows the effect of PGG treatment for 15 minutes or 24 hours on MDCK I cell hyaluronan expression by Western blot.

As shown in FIG. 6A, PGG treatment for 15 minutes or 24 hours attenuated hyaluronan expression (red color) on the surface of wounded MDCK 1 cells in a concentration dependent manner, when observed under confocal microscopy. When these changes were evaluated semi quantitatively using Western blot, total cell hyaluronan expression by the wounded monolayers was decreased within 15 minutes of PGG addition (FIG. 6B). These effects persisted and were slightly more pronounced across all concentration ranges (1-10 μM) after 24 hours exposure (FIG. 6B). Therefore, PGG appears to decrease cell surface hyaluronan exposure quickly and persistently, and this effect is one potential pathway whereby PGG might exert it anti-adhesion property.

Example 5

Toxicology Study

Figure 7:
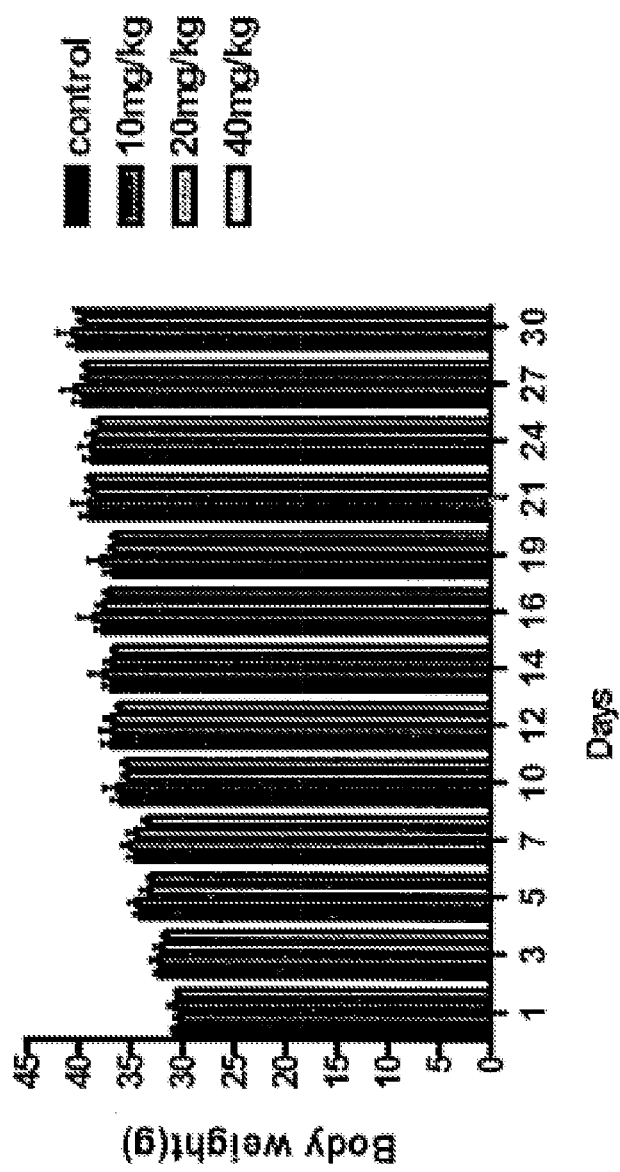
FIG. 7 illustrates the effect of PGG on the body weight of mice.
Figure 8:
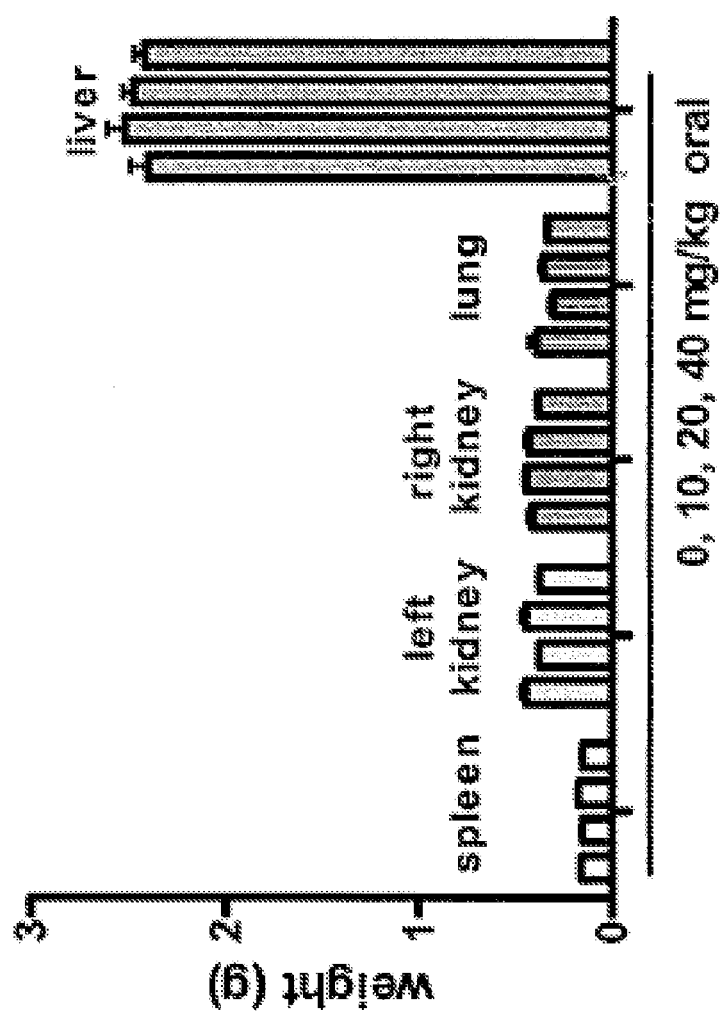
FIG. 8 details the effect of PGG on the organ weight of mice.
Figure 9:
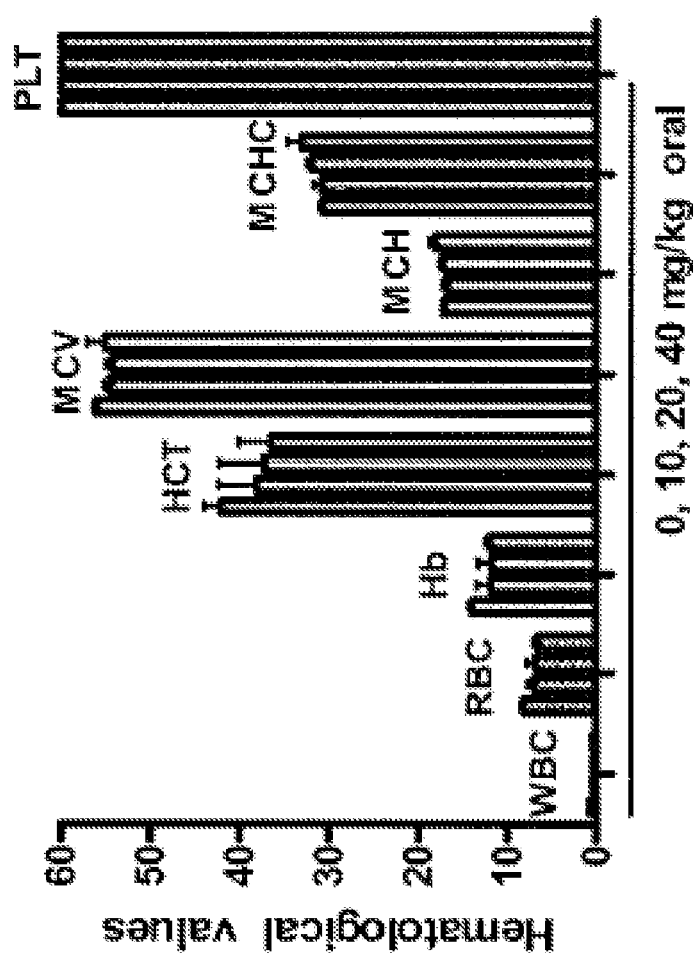
FIG. 9 shows the effect of PGG on hematological values.
Figure 10:
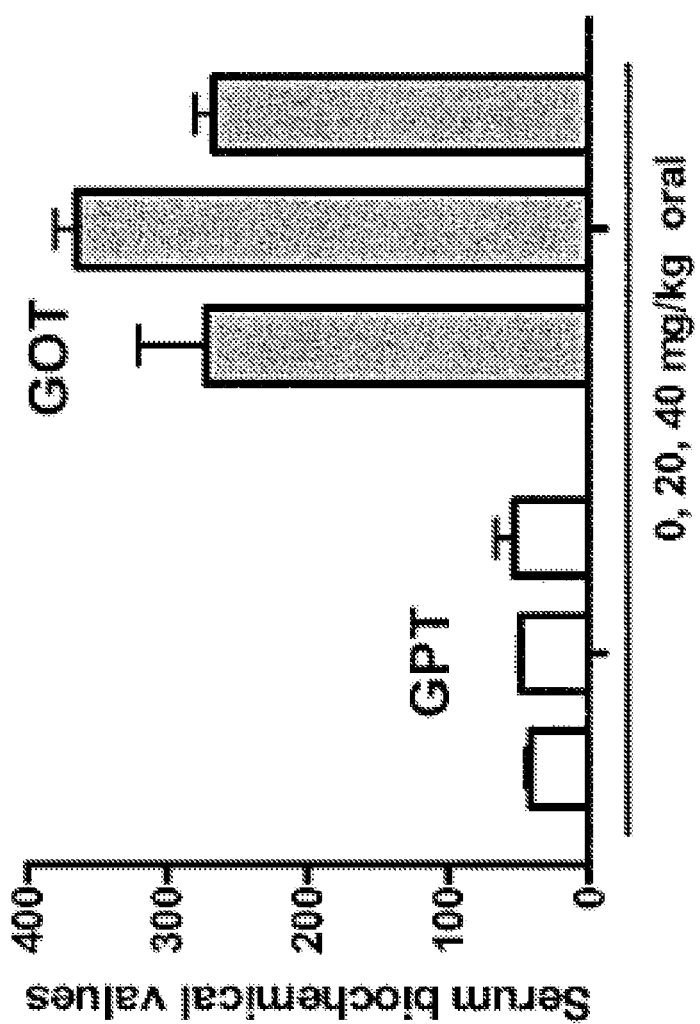
FIG. 10 illustrates the effect of PGG on GOT and GPT levels in mice.
Figure 11:
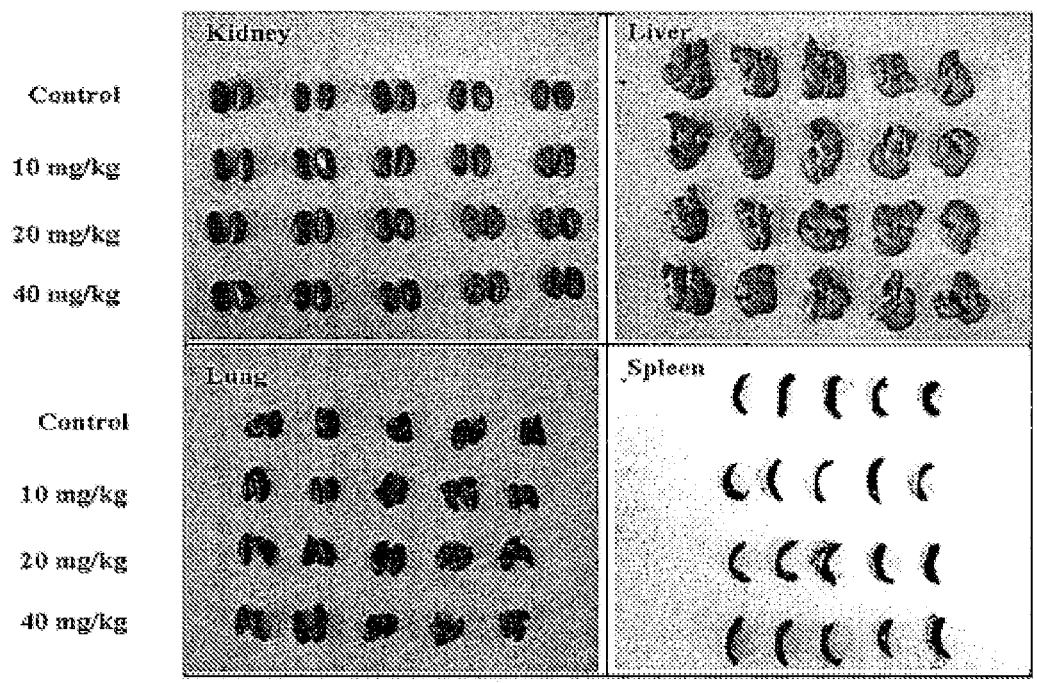
FIG. 11 details the effect of PGG on the morphological features of organs and peritoneal shapes in mice.
Figure 11:
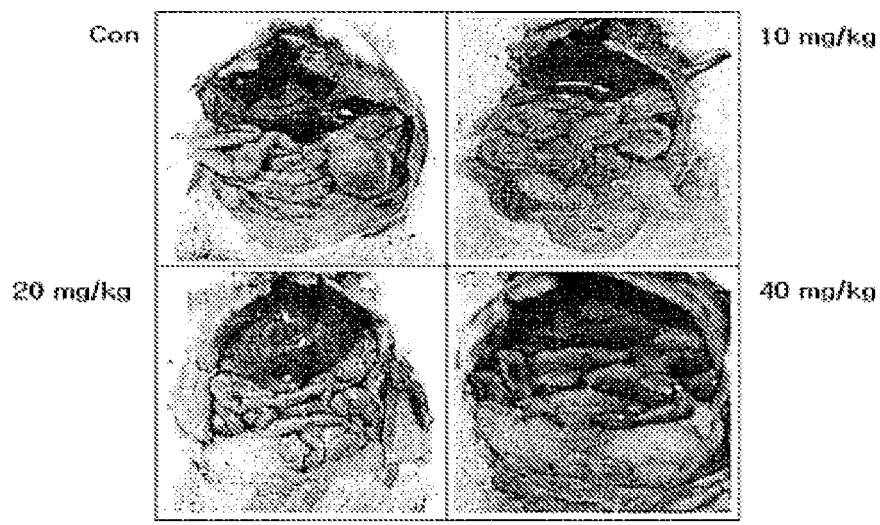

To examine the optimal dose for animal study, a toxicology study was performed in mice orally fed with PGG (10, 20, and 40 mg/kg). Each group consisted of five ICR mice. As shown in FIG. 7, there was no significant difference between the PGG and control groups. Similarly, PGG did not affect the shapes and weights of organs such as the spleen, liver, kidney and lung of the mice (FIGS. 8 and 11). PGG also did not affect the statistical differences of hematological values between the groups (FIG. 9). In addition, PGG did not affect GOT and GPT levels in the mice (FIG. 10).

Example 6

The Effect of PGG on Renal Susceptibility to COM Crystal Deposition in Hyperoxaluric Wild Type Rats Rats were administered PGG, with and without ethylene glycol given to render the rats hyperoxaluric. The effect of PGG on renal crystal deposition was assessed, to confirm the ability of PGG to prevent crystal deposition. Urine of animals was collected and extensively studied to quantitate biochemical and functional changes, and determine the mechanism of the apparent salutary effects, in several studies outlined in Table 1. Functional effects of treated rat urine on crystal nucleation, growth, aggregation and cell interaction was also tested, and compared to urine from control animals.

Six rats per group were treated (see Table 1 below). Harlan Sprague Dawley Rats (300 g) received 0.8% ethylene glycol and 1% ammonium chloride mixed with the drinking water to induce nephrolithiasis, PGG in 2 different doses (4 mg/kg and 20 mg/kg), or both for a full 4 weeks. The doses of PGG covered the range deemed effective in mouse experiments on angiogenesis over a 2-log range factored for relative body size. PGG was administered to all rats via lavage. Urine was collected for chemistries and crystalluria quantification at weekly intervals, with full urinary inhibition studies at 3 weeks, and histologic evaluation after week 3. Kidneys were examined quantitatively for the presence of cortical and medullary crystals, as well as interstitial fibrosis, by a blinded observer. Crystal deposition within cortex and medulla were also quantified under polarizing microscopy using Metamorph software.

TABLE 1

Experimental design.

| Groups | Week 1 | Week 2 | Week 3 |
|---|---|---|---|
| Control | U, C | U, C | U, C |
| EG × 3 wks | U, C | U, C | U, C |
| PGG1 + EG × 3 wks | U, C | U, C | U, C |
| PGG2 + EG × 3 wks | U, C | U, C | U, C |

U: Urine chemistries (pH, volume, citrate, Ca, Ox, Mg, UA)
I: Inhibition studies (ULM CaOx, ULM CaP, Crystal growth inhibition, Aggregation inhibition, cell-crystal interactions; for these studies the urine of rats was collected in metabolic cages; urine from different days during each week of study was used to complete each of the parameters as necessary)
H: Renal histology
C: Crystalluria
EG: 0.8% ethylene glycol and 1% ammonium chloride mixed with the drinking water
PGG1: PGG dose 1 (4 mg/kg)
PGG2: PGG dose 2 (20 mg/kg)

General Methods

Crystalluria.

Twenty four-hour rat urine samples were collected in a metabolic cage with sodium azide as a preservative. Urine was centrifuged, the pellet resuspended, and crystal size and quantity assessed in a hemocytometer.

Detection and analysis of renal calcium deposits and stones, fibrosis, and tissue oxidant status. For histochemical detection of spontaneous renal calcinosis in rats, kidneys were freshly dissected. For each animal, one kidney was snap-frozen in liquid nitrogen (for crystal identification and other studies that require unfixed tissue), and the other fixed in 10% buffered formalin and paraffin-embedded for histology. Five micrometer-thick sagittal sections were cut, deparaffinized and stained with a von Kossa procedure that specifically detects calcium deposits. After a brief counterstaining with 1% neutral red, the slides were viewed by light microscopy and scored by a blinded observer to score interstitial fibrosis and crystallization on a semi-quantitative scale.

Expression of Renal Tubular Cell Crystal Binding Moieties.

Renal tissue sections were stained for HA, OPN, CD44 and Annexin II (AxII). Fixed tissue sections were blocked with 1% BSA for HA and with normal horse serum for OPN, CD44 and AxII staining and incubated with primary labels (biotinylated HA-binding protein, Seikagaku, Falmouth, Md.; mouse monoclonal antihuman OPN antibody (University of Delaware; mouse anti-human CD44 antibody, Bender MedSystems, Vienna, Austria); mouse anti-AxII (BD Transduction Labs, Franklin Lakes, N.J.); or mouse anti-nucleolin (MBL Co. Ltd., Japan). For OPN, CD44, AxII, or nucleolin sections were subsequently incubated with secondary labels, biotinylated horse anti-goat and horse anti-mouse antibodies (Vector Laboratories, Burlingame, Calif.). Finally, avidin-biotin peroxidase complex (Vector) and diaminobenzidine were used to detect HA, OPN, AxII, nucleolin and CD44. Sections were counterstained with methyl green. Controls were run to verify lack of staining when primary labels were omitted. Corticomedullary cross sections of the kidney (1 per animal) were examined randomly by a computer-aided image analysis program (MetaMorph, Meta ImagingSeries 4.6). In each representative slide, staining was semi-automatically quantified in 15 to 20 fields, expressed as percentage of staining of total surface area, and the results from all fields were averaged. HA was not quantified in the medulla because of the well-known abundant amount of HA in the interstitium of the inner medulla stains nearly the entire tissue.

Fibrosis and Apoptosis Scoring.

Fixed blocks of tissue were embedded in paraffin, and 5 µm-thick sections cut from each block. The sections were then stained with trichrome and Sirius red. Corticomedullary cross sections of the kidney (1 per animal) were examined randomly by a computer-aided image analysis program (MetaMorph, Meta Imaging Series 4.6). In each representative slide, staining was semi automatically quantified in 15 to 20 fields, expressed as percentage of staining of total surface area, and the results from all fields were averaged. Apoptotic signs were characterized in renal cells with the TUNEL method (ApopTag peroxidase in situ apoptosis detection kit, Serologicals Corp). Apoptotic cells were quantified in 15 fields as the percentage of TUNEL positive nuclei in each field.

Urinalysis.

Spot urine or 24-hr urine samples from individual rats under study were assayed before and after hyperoxaluric treatment. Spot urine samples were collected directly into Eppendorf tubes, centrifuged at 5,000×g for 5 min to dispose of cell debris, and stored at −80° C. until use. Urinary concentrations of oxalate, calcium and other determinants of SS were measured. SS was calculated using the EQUIL2 program.

Power.

This study included 6 animals in each experimental group (Table 1). Given the variability for urine chemistries noted in previous rat studies using HP, this gave us 80% power to detect differences in group means of approximately 20% for standard urine chemistries. For semi-quantitative histologic analyses of renal crystallization, given a baseline of nearly 100% of HP-treated rats effected with crystals, we had the power to detect a difference of percentage effected as small as approximately 20%. For quantitative histologic parameters, e.g., renal fibrosis scoring, power was better and paralleled that for the urine chemistries or urinary markers.

Urine chemistry and enzymes were evaluated to measure urine pH, creatine clearance, the presence and concentration of oxalate, calcium, citrate, and 8-Hydroxy-2'-deoxyguanosine (8-OH-dG). 8-OH-dG has been regarded as a potential marker of oxidative DNA damage induced by ROS. Urinary 8-OHdG was measured using a commercially available competitive 8-OHdG enzyme-linked immunosorbent assay kit. The number of oxalate crystal deposits in the kidneys was measured using a hematoxylin and eosin stain. Reverse transcriptase PCR (RT-PCR) was used to detect and quantify superoxide dismutase (SOD) mRNA and osteopontin mRNA. Immunohistochemical staining techniques were used to measure SOD and osteopontin protein expression of hyaluronan. Blood chemistry was also studied to measure levels of creatinine, uric acid, phosphate, blood urea nitrogen (BUN), and malondialdehyde (MDA) in the subjects.

Similar methods to those described above have been utilized in similar studies. See, for example, Jeong, B. C. et al., *J. Endourol.* 20(5):356-61 2006; Itoh, Y. et al., *J. Urol.* 173 (1):271-5 2005; Tsujihata, M. et al., *J. Urol.* 180(5):2212-7 2008; Ahn, S. H., et al., *Korean J. Urol.* 44(1):87-94 2005.

Results.

Serum chemistries were measured and the results are detailed in Table 2.

TABLE 2

| Serum Chemistries (mean serum ± SD (mg/dl)) | | | |
|---|---|---|---|
| | Normal | Stone | PGG 4 mg/kg | PGG 20 mg/kg |
| Creatinine | 0.6 ± 0.1 | 0.9 ± 0.5 | 0.6 ± 0.5 | 0.6 ± 0.1 |
| BUN | 15.3 ± 0.5 | 25.3 ± 5.2 | 24.6 ± 3.9 | 23.3 ± 3.7 |
| Uric acid | 3.9 ± 3.9 | 2.6 ± 2.5 | 2.9 ± 3.2 | 1.6 ± 1.0 |
| Calcium | 10.1 ± 0.5 | 11.1 ± 1.0 | 10.9 ± 1.1 | 10.5 ± 0.3 |
| Phosphate | 10.5 ± 1.8 | 11.5 ± 1.0 | 10.7 ± 1.4 | 9.4 ± 0.8 |

Results for the urine chemistry measurements are shown in Table 3.

TABLE 3

| Urine Chemistries | | | |
|---|---|---|---|
| | Normal | Stone | PGG 4 mg/kg | PGG 20 mg/kg |
| Mean Vol ± SD (ml) | 35.3 ± 2.44 | 39.5 ± 1.0 | 33.0 ± 3.74 | 34.7 ± 3.59 |
| Mean pH ± SD | 6.8 ± 0.4 | 7.8 ± 1.0 | 6.7 ± 1.2 | 7.1 ± 0.8 |
| Calcium | 2.95 ± 0.92 | 3.85 ± 1.9 | 2.95 ± 0.31 | 3.52 ± 0.31 |

Figure 12:
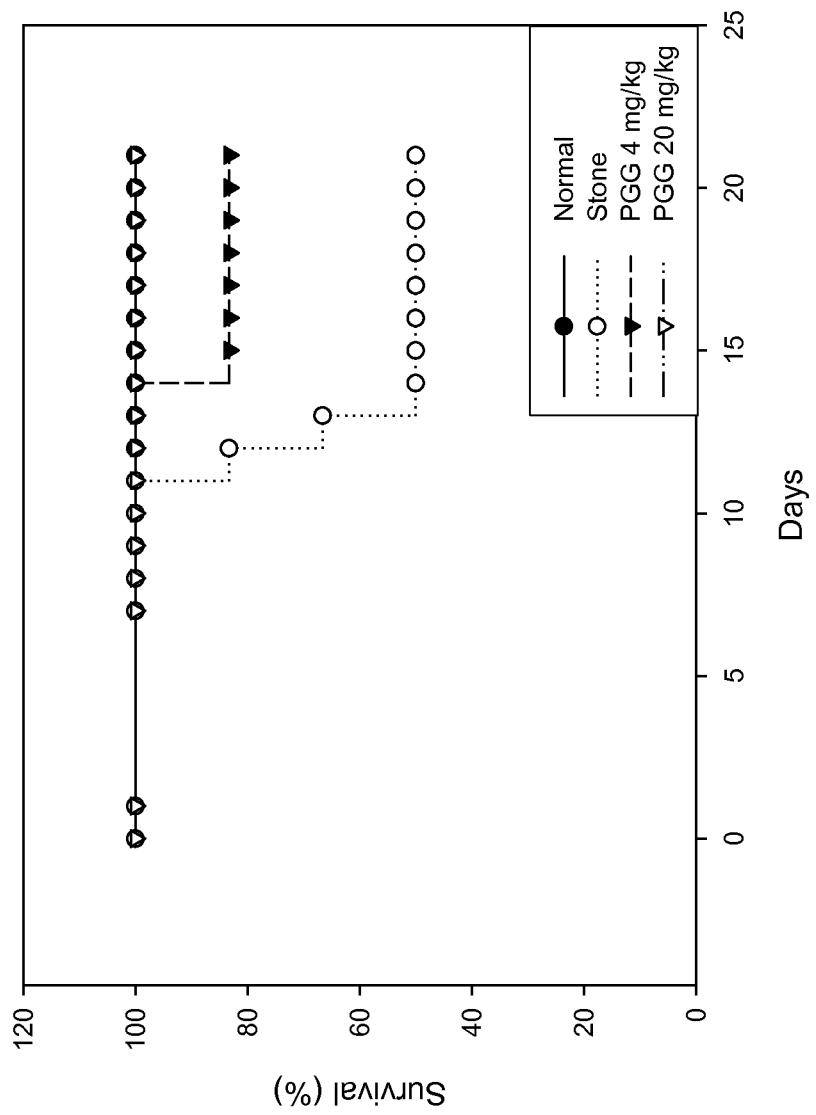
FIG. 12 illustrates the effect of PGG on the mortality of rats studied.

As shown in FIG. 12 and Table 4, the survival time of the rats in the study were increased upon administration of PGG. In fact, the rates administered 20 mg/kg PGG had a survival rate that mirrored that of those in the normal group.

TABLE 4

| Effect of PGG on the mortality of rats studied. | |
|---|---|
| Groups | Survival (%) |
| Normal | 100% |
| Stone | 50% |
| PGG 4 mg/kg | 83% |
| PGG 20 mg/kg | 100% |

Figure 13:
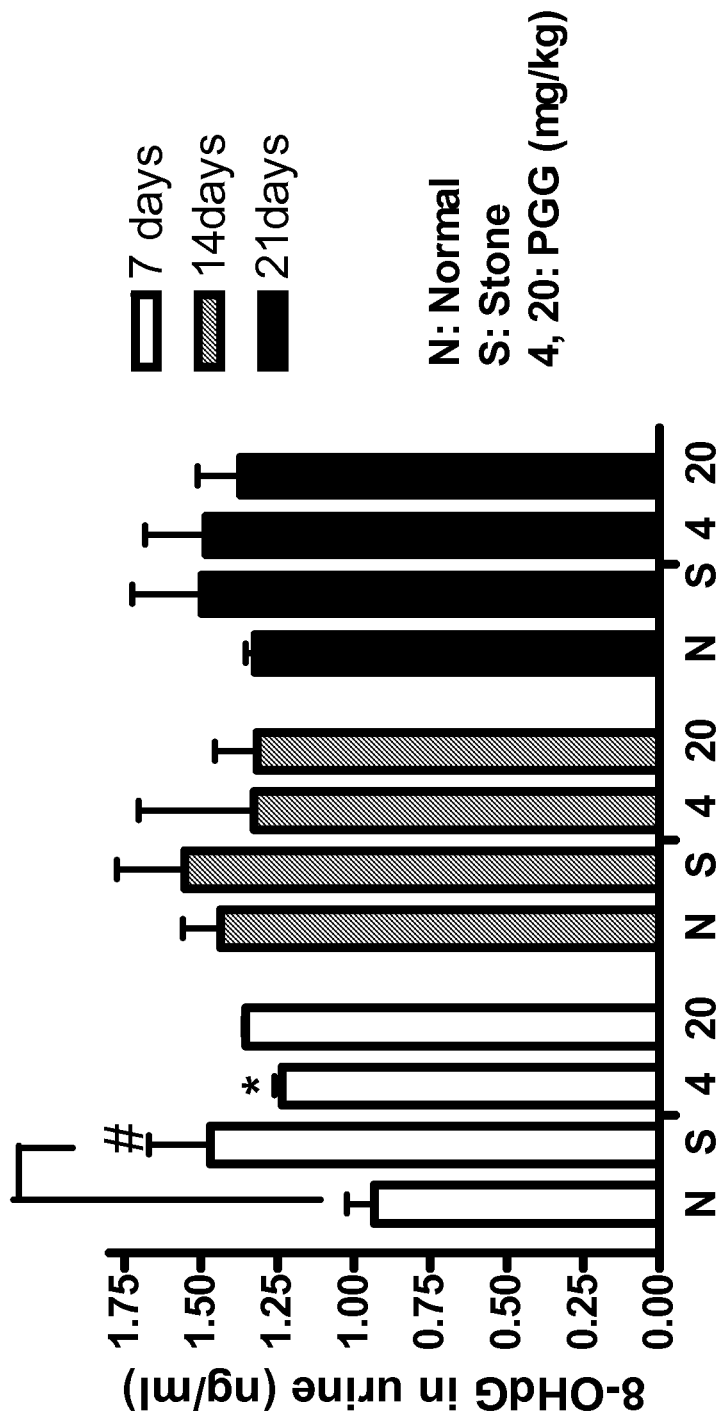
FIG. 13 details the effect of PGG on 8-OHdG levels in urine.
Figure 14:
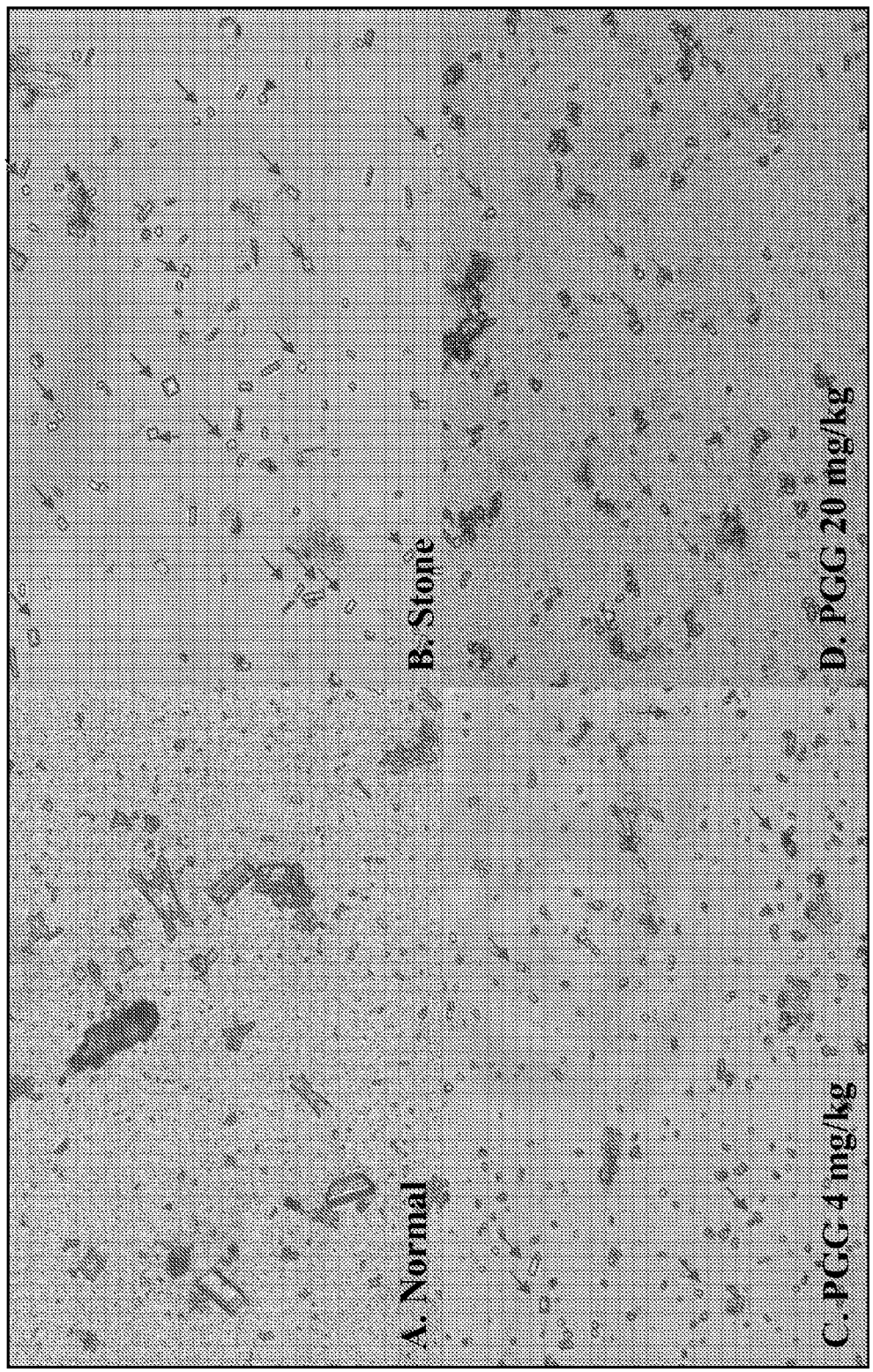
FIG. 14 shows the presence of calcium oxalate in urine at 21 days.
Figure 15:
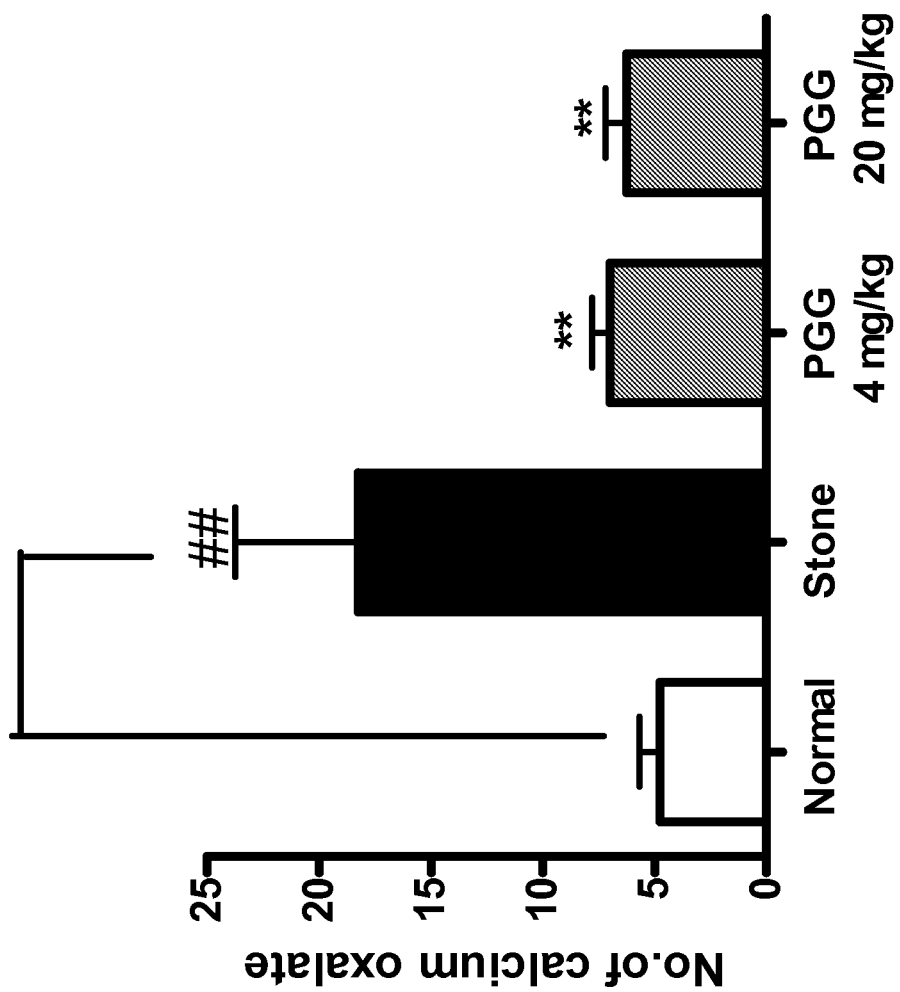
FIG. 15 illustrates the number of calcium oxalate crystalluria found in urine at 21 days.
Figure 16:
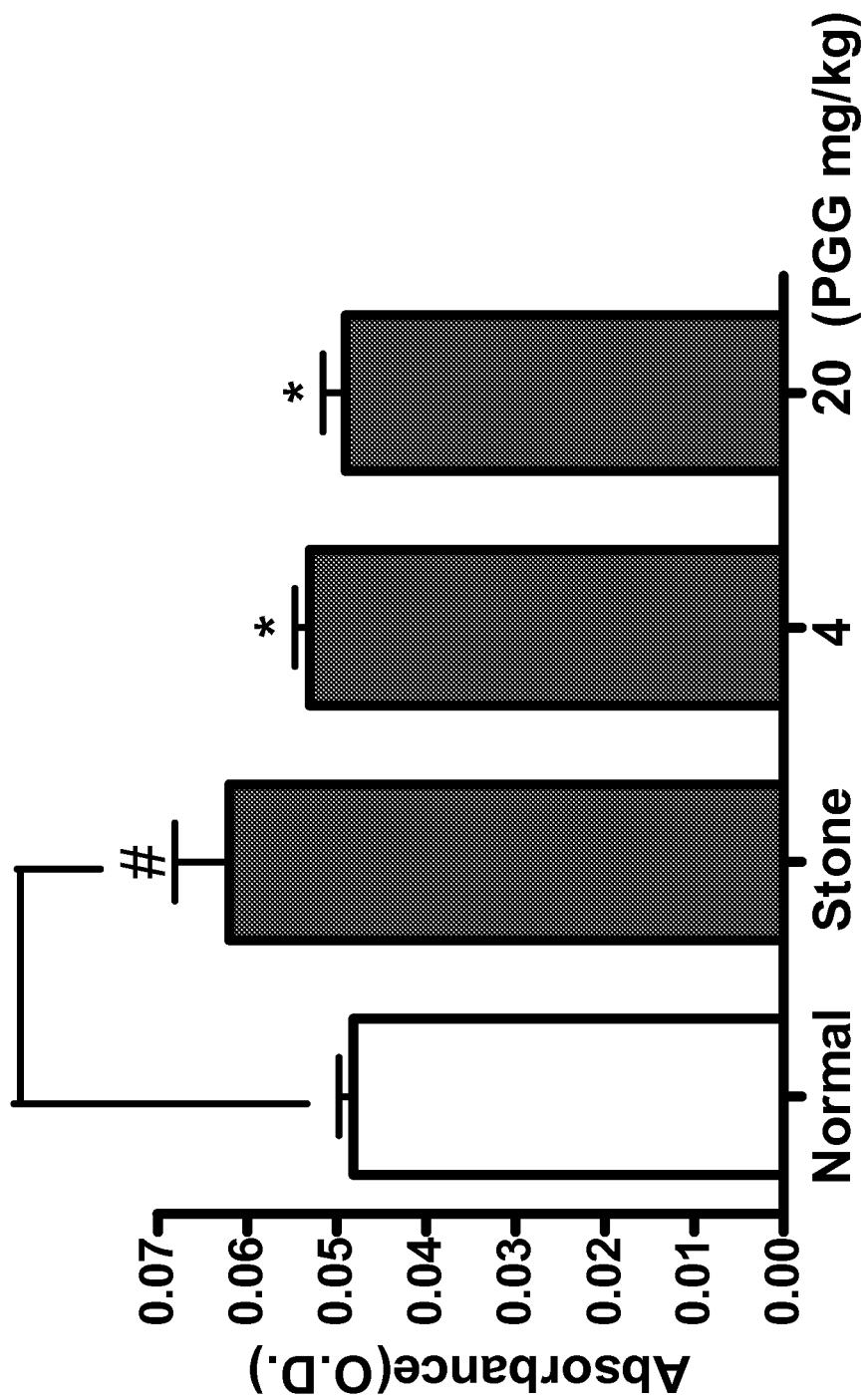
FIG. 16 shows the effect of PGG on MDA in serum.

FIG. 13 details the effect of PGG on 8-OHdG levels in urine. Values represent the means±S.D.; # represents p<0.05 versus the normal group; and * represents P<0.05 versus the stone group. As shown in FIG. 14, the number of stones present in the PGG rats was considerably less than those in the stone group, indicating the protective qualities of PGG. The images are shown with tetragonal bipyramidal habit (400×). FIG. 15 details the number of calcium oxalate (CaOx) crystalluria present in each group. The results were obtained by counting the number of CaOx per 400× power field observation. Values represent the means±S.D.; # represents p<0.01 versus the normal group; and * represents P<0.01 versus the stone group. Again, the PGG samples have values which are similar to those observed in the normal group. The results of the Malondialdehyde (MDA) assay are shown in FIG. 16 and are indicative of the effect of PGG on MDA in serum. As above, the values represent the means±S.D.; # represents p<0.05 versus the normal group; and * represents P<0.05 versus the stone group.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method of reducing binding of renal calculi to renal cells in a subject in need thereof, the method comprising administering to the subject a therapeutically effective amount of 1,2,3,4,6-penta-O-galloyl-beta-D-glucose, or a salt thereof.

2. The method of claim 1, wherein the renal calculi comprises one or more of calcium oxalate, struvite, urate, calcium phosphate, cystine, silicate, xanthine, and triamterene.

3. The method of claim 2, wherein the calcium oxalate is selected from calcium oxalate monohydrate and calcium oxalate dihydrate.

4. The method of claim 3, wherein the calcium oxalate is calcium oxalate monohydrate.

5. The method of claim 1, wherein the renal cells are selected from renal epithelial cells and renal endothelial cells.

6. The method of claim 5, wherein the renal cells are renal epithelial cells.

7. The method of claim 6, wherein the renal epithelial cells are renal tubular epithelial cells.

8. The method of claim 1, wherein the renal cells are proliferating.

9. The method of claim 1, wherein the renal cells are migrating.

10. The method of claim 1, wherein the renal cells are under oxalate-induced peroxidative injury.

11. The method of claim 1, wherein the renal cells are wound damaged.

12. The method of claim 1, wherein the 1,2,3,4,6-penta-O-galloyl-beta-D-glucose reduces hyaluronan expression in the renal cells.

13. The method of claim 12, wherein the hyaluronan expression is cell-surface expression.

14. A method of treating a subject having nephrolithiasis, the method comprising administering to the subject a therapeutically effective amount of 1,2,3,4,6-penta-O-galloyl-beta-D-glucose, or a salt thereof.

15. A method of treating a subject having urolithiasis, the method comprising administering to the subject a therapeutically effective amount of 1,2,3,4,6-penta-O-galloyl-beta-D-glucose, or a salt thereof.

16. A method of reducing hyaluronan expression in renal cells in a subject, having renal calculi the method comprising administering to the subject a therapeutically effective amount of 1,2,3,4,6-penta-O-galloyl-beta-D-glucose, or a salt thereof.

17. The method of claim 16, wherein the hyaluronan is expressed on the cell surface.

18. The method of claim 16, wherein the renal cells are selected from renal epithelial cells and renal endothelial cells.

19. The method of claim 18, wherein the renal cells are renal epithelial cells.

20. The method of claim 19, wherein the renal epithelial cells are renal tubular epithelial cells.

21. The method of claim 16, wherein the renal cells are proliferating.

22. The method of claim 17, wherein the renal cells are migrating.

23. The method of claim 16, wherein the renal endothelial cells are under oxalate-induced peroxidative injury.

24. The method of claim 16, wherein the renal endothelial cells are wound damaged.

25. A method of reducing proliferative and/or migratory activity of renal cells in a subject having renal calculi, the method comprising administering to the subject a therapeutically effective amount of 1,2,3,4,6-penta-O-galloyl-beta-D-glucose, or a salt thereof.

26. The method of claim 25, wherein the migratory activity is repair migration.

27. The method of claim 25, wherein the proliferative and/or migratory activity is activated by physical injury.

* * * * *